United States Patent
Lo et al.

(10) Patent No.: US 12,180,549 B2
(45) Date of Patent: *Dec. 31, 2024

(54) DIAGNOSING FETAL CHROMOSOMAL ANEUPLOIDY USING GENOMIC SEQUENCING

(75) Inventors: Yuk-Ming Dennis Lo, Kowloon (HK); Rossa Wai Kwun Chiu, New Territories (HK); Kwan Chee Chan, Kowloon (HK)

(73) Assignee: The Chinese University of Hong Kong, New Territories (HK)

( * ) Notice: Subject to any disclaimer, the term of this patent is extended or adjusted under 35 U.S.C. 154(b) by 4573 days.

This patent is subject to a terminal disclaimer.

(21) Appl. No.: 12/614,350

(22) Filed: Nov. 6, 2009

(65) Prior Publication Data

US 2010/0112590 A1    May 6, 2010

Related U.S. Application Data

(63) Continuation-in-part of application No. 12/178,181, filed on Jul. 23, 2008.

(60) Provisional application No. 60/951,438, filed on Jul. 23, 2007.

(51) Int. Cl.
| | | |
|---|---|---|
| G01N 33/50 | (2006.01) | |
| C12Q 1/6809 | (2018.01) | |
| C12Q 1/6827 | (2018.01) | |
| C12Q 1/6874 | (2018.01) | |
| C12Q 1/6883 | (2018.01) | |
| C12Q 1/6886 | (2018.01) | |
| G16B 20/00 | (2019.01) | |
| G16B 20/10 | (2019.01) | |
| G16B 20/20 | (2019.01) | |
| G16B 30/00 | (2019.01) | |
| G16B 30/10 | (2019.01) | |

(52) U.S. Cl.
CPC ......... *C12Q 1/6886* (2013.01); *C12Q 1/6809* (2013.01); *C12Q 1/6827* (2013.01); *C12Q 1/6874* (2013.01); *C12Q 1/6883* (2013.01); *G16B 20/00* (2019.02); *G16B 20/10* (2019.02); *G16B 20/20* (2019.02); *G16B 30/00* (2019.02); *G16B 30/10* (2019.02); *C12Q 2600/156* (2013.01)
USPC ......................................................... 702/19

(58) Field of Classification Search
None
See application file for complete search history.

(56) References Cited

U.S. PATENT DOCUMENTS

| | | |
|---|---|---|
| 5,641,628 A | 6/1997 | Bianchi |
| 5,879,883 A | 3/1999 | Benson et al. |
| 6,100,029 A | 8/2000 | Lapidus et al. |
| 6,143,496 A | 11/2000 | Brown et al. |
| 6,214,558 B1 | 4/2001 | Shuber et al. |
| 6,258,540 B1 | 7/2001 | Lo et al. |
| 6,391,559 B1 | 5/2002 | Brown et al. |
| 6,440,706 B1 | 8/2002 | Vogelstein et al. |
| 6,566,101 B1 | 5/2003 | Shuber et al. |
| 6,632,655 B1 | 10/2003 | Mehta et al. |
| 6,664,056 B2 | 12/2003 | Lo et al. |
| 6,753,147 B2 | 6/2004 | Vogelstein et al. |
| 6,927,028 B2 | 8/2005 | Dennis et al. |
| 7,332,277 B2 | 2/2008 | Dhallan |
| 7,442,506 B2 | 10/2008 | Dhallan |
| 7,476,363 B2 | 1/2009 | Unger et al. |
| 7,645,576 B2 | 1/2010 | Lo et al. |
| 7,655,399 B2 | 2/2010 | Cantor et al. |
| 7,704,687 B2 | 4/2010 | Wang et al. |
| 7,727,720 B2 | 6/2010 | Dhallan et al. |
| 7,838,647 B2 | 11/2010 | Hahn et al. |
| 7,888,017 B2 | 2/2011 | Quake et al. |
| 8,008,018 B2 | 8/2011 | Quake et al. |
| 2001/0051341 A1 | 12/2001 | Lo et al. |
| 2002/0164816 A1 | 11/2002 | Quake |
| 2003/0022207 A1 | 1/2003 | Balasubramanian et al. |

(Continued)

FOREIGN PATENT DOCUMENTS

| | | |
|---|---|---|
| EP | 0994963 B1 | 5/2003 |
| EP | 2161347 | 3/2010 |

(Continued)

OTHER PUBLICATIONS

"Separation of RNA & DNA by Gel Filtration Chromatography," Edvotek, 1987, pp. 1-9.
Al Sheng Xiong, et al., "A simple, rapid, high-fidelity and cost-effective PCR-based two-step DNA synthesis method for long gene sequences," Nucleic Acids Research, Apr. 19, 2004, vol. 32, No. 12, 10 pages.
B. Zimmermann, et al., "Novel Real-Time Quantitative PCR Test for Trisomy 21," Jan. 1, 2002, Clinical Chemistry, American Association for Clinical Chemistry, vol. 48, No. 2, pp. 362-363.
Barbara Pertl, et al., "Fetal DNA in Maternal Plasma: Emerging Clinical Applications," Obstetrics and Gynecology, Sep. 2001, vol. 98, No. 3, pp. 483-490.
B. Zimmermann, "Molecular Diagnosis in Prenatal Medicine," Ph.D. Thesis, 2004, Only Chapter 1 (Introduction), pp. 1-19.

(Continued)

*Primary Examiner* — Larry D Riggs, II
*Assistant Examiner* — Nidhi Dharithreesan
(74) *Attorney, Agent, or Firm* — Finnegan, Henderson, Farabow, Garrett & Dunner, LLP

(57) ABSTRACT

Embodiments of this invention provide methods, systems, and apparatus for determining whether a fetal chromosomal aneuploidy exists from a biological sample obtained from a pregnant female. Nucleic acid molecules of the biological sample are sequenced, such that a fraction of the genome is sequenced. Respective amounts of a clinically-relevant chromosome and of background chromosomes are determined from results of the sequencing. The determination of the relative amounts may count sequences of only certain length. A parameter derived from these amounts (e.g. a ratio) is compared to one or more cutoff values, thereby determining a classification of whether a fetal chromosomal aneuploidy exists. Prior to sequencing, the biological sample may be enriched for DNA fragments of a particular sizes.

25 Claims, 20 Drawing Sheets

(56) References Cited

U.S. PATENT DOCUMENTS

| | | |
|---|---|---|
| 2003/0044388 A1 | 3/2003 | Dennis et al. |
| 2003/0186255 A1 | 10/2003 | Williams et al. |
| 2003/0204331 A1 | 10/2003 | Whitney et al. |
| 2004/0096892 A1 | 5/2004 | Wang et al. |
| 2004/0137470 A1 | 7/2004 | Dhallan |
| 2004/0203037 A1 | 10/2004 | Lo et al. |
| 2004/0209299 A1 | 10/2004 | Pinter et al. |
| 2005/0003351 A1 | 1/2005 | Fejgin et al. |
| 2005/0019792 A1 | 1/2005 | McBride et al. |
| 2005/0037388 A1 | 2/2005 | Antonarakis et al. |
| 2005/0129581 A1 | 6/2005 | McBride et al. |
| 2005/0145496 A1 | 7/2005 | Goodsaid et al. |
| 2005/0164241 A1 | 7/2005 | Hahn et al. |
| 2005/0221341 A1 | 10/2005 | Shimkets et al. |
| 2005/0221373 A1 | 10/2005 | Enzelberger et al. |
| 2005/0252773 A1 | 11/2005 | McBride et al. |
| 2006/0046258 A1 | 3/2006 | Lapidus et al. |
| 2006/0051775 A1 | 3/2006 | Bianchi et al. |
| 2006/0121452 A1 | 6/2006 | Dhallan |
| 2006/0252068 A1 | 11/2006 | Lo et al. |
| 2006/0252071 A1 | 11/2006 | Lo et al. |
| 2007/0059680 A1 | 3/2007 | Kapur et al. |
| 2007/0134658 A1 | 6/2007 | Bohmer et al. |
| 2007/0202525 A1* | 8/2007 | Quake et al. ............... 435/6 |
| 2007/0207466 A1 | 9/2007 | Cantor et al. |
| 2007/0212689 A1 | 9/2007 | Bianchi et al. |
| 2007/0238105 A1 | 10/2007 | Barrett et al. |
| 2007/0275402 A1 | 11/2007 | Lo et al. |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton et al. |
| 2008/0071076 A1 | 3/2008 | Hahn et al. |
| 2008/0090239 A1 | 4/2008 | Shoemaker et al. |
| 2008/0096216 A1 | 4/2008 | Quake |
| 2008/0096766 A1 | 4/2008 | Lee |
| 2008/0113358 A1 | 5/2008 | Kapur |
| 2008/0124721 A1 | 5/2008 | Fuchs |
| 2008/0138809 A1 | 6/2008 | Kapur et al. |
| 2008/0153090 A1 | 6/2008 | Lo et al. |
| 2008/0182261 A1 | 7/2008 | Bianchi |
| 2008/0193927 A1 | 8/2008 | Mann et al. |
| 2008/0213775 A1 | 9/2008 | Brody et al. |
| 2008/0220422 A1 | 9/2008 | Shoemaker et al. |
| 2008/0299562 A1 | 12/2008 | Oeth et al. |
| 2009/0170114 A1 | 7/2009 | Quake et al. |
| 2009/0280492 A1 | 11/2009 | Stoughton et al. |
| 2009/0291443 A1 | 11/2009 | Stoughton et al. |
| 2010/0094562 A1 | 4/2010 | Shohat et al. |
| 2010/0112575 A1 | 5/2010 | Fan et al. |
| 2010/0216151 A1 | 8/2010 | Lapidus et al. |
| 2010/0216153 A1 | 8/2010 | Lapidus et al. |
| 2010/0291572 A1 | 11/2010 | Stoughton et al. |
| 2011/0003293 A1 | 1/2011 | Stoughton et al. |

FOREIGN PATENT DOCUMENTS

| | | |
|---|---|---|
| WO | 03020974 | 3/2003 |
| WO | WO2003/030823 | 4/2003 |
| WO | 03048295 A1 | 6/2003 |
| WO | 2004065629 | 8/2004 |
| WO | WO2004/065629 A1 | 8/2004 |
| WO | WO2004/078999 A1 | 9/2004 |
| WO | 2005023091 | 3/2005 |
| WO | WO 2005118852 | 12/2005 |
| WO | WO 2006010610 A2 | 2/2006 |
| WO | WO 2006108101 | 10/2006 |
| WO | WO2007/028155 A2 | 3/2007 |
| WO | WO 2007044091 A2 | 4/2007 |
| WO | WO 2007075836 | 7/2007 |
| WO | WO2007/092473 A2 | 8/2007 |
| WO | WO2007/100911 A2 | 9/2007 |
| WO | WO 2007132166 | 11/2007 |
| WO | WO 2007132167 | 11/2007 |
| WO | WO2007/147073 A2 | 12/2007 |
| WO | WO2007/147074 A2 | 12/2007 |
| WO | WO2007/147076 A2 | 12/2007 |
| WO | WO2008/050734 A1 | 5/2008 |
| WO | WO2008/150368 | 12/2008 |
| WO | WO2009/013492 A1 | 1/2009 |
| WO | WO2009/013496 A1 | 1/2009 |
| WO | WO2009/019455 A2 | 2/2009 |
| WO | WO2009/037690 | 3/2009 |

OTHER PUBLICATIONS

Bert Vogelstein, et al., "Digital PCR," Proc. Natl. Acad. Sci. USA, Aug. 1999, vol. 96., pp. 9236-9241.

Chan, et al. "Size Distributions of Maternal and Fetal DNA in Maternal Plasma," Clinical Chemistry, 2004, 50:1, pp. 88-92.

Chiu, et al. Non-invasive prenatal assessment of trisomy 21 by multiplexed maternal plasma DNA sequencing: large scale validity study. BMJ, Dec. 14, 2010, pp. 1-9.

Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51), pp. 20458-20463.

Devin Dressman, et al., "Transforming single DNA molecules into fluorescent magnetic particles for detection and enumeration of genetic variations," PNAS, Jul. 2003, vol. 100, No. 15, pp. 8817-8822.

Dhallan et al., "A non-invasive test for prenatal diagnosis based on fetal DNA present in maternal blood: a preliminary study," The Lancet, Feb. 2, 2007, vol. 369: pp. 474-481.

Elizabeth A. Ottesen, et al., "Microfluidic Digital PCR Enables Multigene Analysis of Individual Environmental Bacteria," Science, Dec. 2006, vol. 314, pp. 1464-1467.

Enders K.O. Ng, et al., "The Concentration of Circulating Corticotropin-releasing Hormone mRNA in Maternal Plasma Is Increased in Preeclampsia," Clinical Chemistry, 2003, vol. 49, No. 5, pp. 727-731.

EPO Examination Report, EP Application No. 07 763 674.4, Dec. 21, 2010, 3 pages.

EPO Search Report, EP Application No. 07 763 674.4, Jul. 31, 2009, 10 pages.

Eugene Y. Chan, et al., "DNA Mapping Using Microfluidic Stretching and Single-Molecule Detection of Fluorescent Site-Specific Tags," Genome Research, 2004, vol. 14, pp. 1137-1146.

European search report dated Dec. 21, 2009 for Application No. 07798579.4, 3 pages.

European search report dated Dec. 22, 2009 for Application No. 07798580.2, 3 pages.

European search report dated Dec. 22, 2009 for Application No. 07784444.7, 4 pages.

European search report dated Nov. 9, 2009 for Application No. 7784442.1, 3 pages.

European Examination report dated Jul. 13, 2010 issued in related EP application No. 08776043.5.

Fiona M. F. Lun, et al., "Microfluidics Digital PCR Reveals a Higher than Expected Fraction of Fetal DNA in Maternal Plasma," Clinical Chemistry, 2008, vol. 54, No. 10, pp. 1664-1672.

Frank Diehl, et al., "Digital quantification of mutant DNA in cancer patients," Curr Opin Oncol, 2007, 19, pp. 36-42.

H. Christina Fan, et al., "Detection of Aneuploidy with Digital Polymerase Chain Reaction," Analytical Chemistry, Oct. 1, 2007, vol. 79, No. 19, pp. 7576-7579.

H. Christina Fan, et al., "Microfluidic digital PCR enables rapid prenatal diagnosis of fetal aneuploidy," American Journal of Obstetrics & Gynecology, May 2009, pp. 543e1-543-e7.

H. Christina Fan, et al., "Noninvasive diagnosis of fetal aneuploidy by shotgun sequencing DNA from maternal blood," PNAS, Oct. 21, 2008, vol. 105, 16266-16271.

Haissam Rahil, et al., Rapid detection of common autosomal aneuploidies by quantitative fluorescent PCR on uncultured amniocytes, European Journal of Human Genetics, 2002, vol. 10, pp. 462-466.

Hong, et al. A nanoliter-scale nucleic acid processor with parallel architecture. Nat. Biotechnol. 2004; 22(4), pp. 435-439.

(56) References Cited

OTHER PUBLICATIONS

Ido Braslavsky, et al., "Sequence information can be obtained from single DNA molecules," PNAS, Apr. 2003, vol. 100, No. 7, pp. 3960-3964.
Ilona Hromadnikova, et al., "Quantitative analysis of DNA levels in maternal plasma in normal and Down syndrome pregnancies," Bio Med Central, May 2002, pp. 1-5.
International preliminary report on patentability dated Oct. 14, 2008 for PCT/US2007/003209, 7 pages.
International Search Report and Written Opinion for PCT/US2007/003209, mailed Sep. 18, 2008.
International Search Report, International Application No. PCT/US09/57136, Mar. 16, 2010, 3 pages.
Jay Shendure, et al., "Next-generation DNA sequencing," Nature, 2008, vol. 26, No. 10, pp. 1135-1145.
Jong Wook Hong, et al., "Molecular biology on a microfluidic chip," Journal of Physics: Condensed Matter, 2006, vol. 18, pp. S691-S701.
Joshua S. Marcus, et al., "Microfluidic Single-Cell mRNA Isolation and Analysis," American Chemical Society, Mar. 2006, pp. A-F.
Joshua S. Marcus, et al., "Parallel Picoliter RT-PCR Assays Using Microfluidics," Analytical Chemistry, Feb. 1, 2006, vol. 78, No. 3, pp. 956-958.
Jouni Uitto, et al., "Probing the fetal genome: progress in non-invasive prenatal diagnosis," Trends in Molecular Medicine, Aug. 2003, vol. 9, No. 8, pp. 339-343.
Jun Zhu, et al., "Single Molecule Profiling of Alternative Pre-mRNA Splicing," Science, Aug. 2003, vol. 301, pp. 836-838.
Kasakov, et al. Extracellular DNA in the blood of pregnant women. Tsitologiia. 1995;37(3):232-6. (English translation only), 7 pages.
Leo L.M. Poon, et al., "Circulating fetal DNA in maternal plasma," Clinical Chimica Acta, 2001, vol. 313, 151-155.
Leutwyler, K., Mapping Chromosomes 21, Scientific American, May 15, 2000, 2 pages.
Maloney, et al., "Microchimerism of Maternal Origin Persists into Adult Life," Journal Clinical Investigation, Jul. 1999, 104, pp. 41-47.
Maureen Martin, et al., "A Method for Using Serum or Plasma as a Source of DNA for HLA Typing," Human Immunology, 1992, vol. 33, pp. 108-113.
Nelson, et al Genotyping fetal DNA by non-invasive means: extraction from maternal plasma. Vox Sanguinis. 2001. 80: pp. 112-116.
Office action (Ex parte Quayle) dated May 13, 2011 for U.S. Appl. No. 11/763,421 with pending claims 8 pages.
Office action dated Dec. 1, 2009 for U.S. Appl. No. 11/763,426 with pending claims, 13 pages.
Office action dated Dec. 3, 2008 for U.S. Appl. No. 11/763,426 with pending claims, 22 pages.
Office action dated Dec. 31, 2009 for U.S. Appl. No. 11/763,421 with pending claims, 16 pages.
Office action dated Feb. 15, 2011 for U.S. Appl. No. 11/763,426 with pending claims, 13 pages.
Office Action dated Jan. 12, 2009 for U.S. Appl. No. 11/763,133 with pending claims, 12 pages.
Office action dated Jul. 10, 2009 for U.S. Appl. No. 11/763,421 with pending claims, 26 pages.
Office action dated Jun. 14, 2010 for U.S. Appl. No. 11 /763,426 with pending claims, 16 pages.
Office action dated Mar. 11, 2010 for U.S. Appl. No. 11/763,245 with pending claims, 19 pages.
Office action dated Mar. 29, 2011 for U.S. Appl. No. 11/763,245 with pending claims, 25 pages.
Office action dated Mar. 4, 2009 for U.S. Appl. No. 11/228,454 with pending claims, 16 pages.
Office action dated May 18, 2011 for U.S. Appl. No. 12/413,467 with pending claims, 39 pages.
Office action dated May 6, 2011 for U.S. Appl. No. 11/763,133 with pending claims, 46 pages.
Office action dated Nov. 3, 2009 for U.S. Appl. No. 11/763,133 with pending claims, 17 pages.
Office action dated Sep. 23, 2009 for EP Application No. EP07763674.4 with pending claims, 5 pages.
P.J. Sykes, et al., "Quantitation of Targets for PCR by Use of Limiting Dilution," BioTechniques, 1992, vol. 13, No. 3, 444-449.
Pohl, et al., "Principle and Applications of Digital PCR," Expert Reviews in Molecular Diagnosis. 2004. 4, pp. 41-47.
Rebecca Sparkes, et al., "New Molecular Techniques for the Prenatal Detection of Chromosomal Aneuploidy," JOGC, Jul. 2008, No. 210, pp. 617-621.
Richard A. White III, et al., "Digital PCR provides sensitive and absolute calibration for high throughput sequencing," BMC Genomics, Mar. 19, 2009, 10:116, 30 pages.
Rossa W.K. Chiu, et al., "Effects of Blood-Processing Protocols on Fetal and Total DNA Quantification in Maternal Plasma," Clinical Chemistry, 2001, vol. 47, No. 9, pp. 1607-1613.
Ryo Kimura, et al., "The DYRK1A gene, encoded in chromosome 21 Down syndrome critical region, bridges between .beta.-amyloid production and tau phosphorylation in Alzheimer disease," Human Molecular Genetics, Nov. 29, 2006, vol. 16, No. 1, pp. 15-23.
Satiroglu Tufan, N. Lale, et al., Analysis of Cell-Free Fetal DNA from Maternal Plasma and Serum Using a Conventional Multiplex PCR: Factors Influencing Success, Turk J Med Sci, 35 (2005) pp. 85-92.
Sehnert, et al. Optimal Detection of Fetal Chromosomal Abnormalities by Massively Parallel DNA Sequencing of Cell-Free Fetal DNA from Maternal Blood. Clin Chem. Apr. 25, 2011, 8 pages [Epub ahead of print].
Sinuhe Hahn, et al., "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, pp. 649-656.
Solexa Genome Analysis System. 2006; 2 pages.
Stuart L. Emanuel, et al., "Amplification of Specific Gene Products from Human Serum," GATA, 1993, vol. 10, No. 6, pp. 144-146.
Tetsuya S. Tanaka, et al., "Genome-wide expression profiling of mid-gestation placenta and embryo using a 15,000 mouse developmental cDNA microarray," PNAS, Aug. 2000, vol. 97, No. 16, pp. 9127-9132.
Tettelin, T., et al., "The nucleotide sequence of *Saccharomyces cerevisiae* chromosome VII," Nature 1997, 387, pp. 81-84.
Vincenzo Cirigliano, et al., "Clinical application of multiplex quantitative fluorescent polymerase chain reaction (QF-PCR) for the rapid prenatal detection of common chromosome aneuploidies," Molecular Human Reproduction, 2001, vol. 7, No. 10, pp. 1001-1006.
Voelkerding, et al. Digital fetal aneuploidy diagnosis by next-generation sequencing. Clin Chem. Mar. 2010;56(3), pp. 336-338.
Y. M. Dennis Lo, et al., "Plasma placental RNA allelic ratio permits noninvasive prenatal chromosomal aneuploidy detection," Nature Medicine, Jan. 2007, 6 pages.
Y. M. Dennis Lo, et al., "Prenatal diagnosis: progress through plasma nucleic acids," Nature, Jan. 2007, vol. 8, pp. 71-76.
Y. M. Dennis Lo, et al., "Presence of fetal DNA in maternal plasma and serum," The Lancet, Aug. 16, 1997, vol. 350, pp. 485-487.
Y.M. Dennis Lo, et al., "Digital PCR for the molecular detection of fetal chromosomal aneuploidy," PNAS, Aug. 7, 2007, vol. 104, No. 32, pp. 13116-13121.
Y.M. Dennis Lo, et al., "Quantitative Analysis of Fetal NA in Maternal Plasma and Serum: Implications for Noninvasive Prenatal Diagnosis," Am J. Hum. Genet., 1998, vol. 62, pp. 768-775.
Ying Li, et al., "Size Separation of Circulatory DNA in Maternal Plasma Permits Ready Detection of Fetal DNA Polymorphisms," 2004, Clinical Chemistry, vol. 50, No. 6, pp. 1002-1011.
Y-M. D. Lo, et al., "Detection of fetal RhD sequence from peripheral blood of sensitized RhD-negative pregnant women," British Journal of Haematology, 1994, vol. 87, pp. 658-660.
Y-M. D. Lo, et al., "Detection of single-copy fetal DNA sequence from maternal blood," The Lancet, Jun. 16, 1990, vol. 335, pp. 1463-1464.
Y-M. D. Lo, et al., "Fetal DNA in Maternal Plasma," Ann. N. Y. Acad. Sci, Apr. 2000, vol. 906, pp. 141-147.

(56) References Cited

OTHER PUBLICATIONS

Y-M. D. Lo, et al., "Prenatal Sex Determination by DNA Amplification from Maternal Peripheral Blood," The Lancet, Dec. 9, 1989, pp. 1363-1365.
Young Ho Yang, et al., "Rapid Prenatal Diagnosis of Trisomy 21 by Real-time Quantitative Polymerase Chain Reaction with Amplification of Small Tandem Repeats and S100B in Chromosome 21," Yonsei Medical Journal, 2005, vol. 46, No. 2, pp. 193-197.
Yuk-Ming Dennis Lo, "Noninvasive prenatal detection of fetal chromosomal aneuploidies by maternal plasma nucleic acid analysis: a review of the current state of the art," BJOG, 2009, vol. 116, pp. 152-157.
Zavala, A., et al., "Genomic GC content prediction in prokaryotes from a sample of genes," Gene 2005, 357(2), pp. 137-143.
G.A. Stolovitzky: "Statistical analysis of MPSS measurements: Application to the study of LPS-activated macrophage gene expression," Proceedings of the National Academy of Sciences, vol. 102, No. 5, Feb. 1, 2005, pp. 1402-1407, XP0055043869, ISSN: 0027-8424, DOI:10.1073/pnas.0406555102 *abstract*.
Meyers Blake C et al: "Analysis of the transcriptional complexity of *Arabidopsis thaliana* by massive parallel signature sequencing," Nature Biotechnology, Nature Publishing Group, New York, NY, US, vol. 22, No. 8, Aug. 1, 2004, pp. 1006-1011, XP002438788, ISSN: 1087-0156, DOI: 10.1038/NBT992 *abstract*.
Extended European Search Report dated Nov. 23, 2012 in European Application No. 12175754.6.
Giurato, et al., "An accurate pipeline for analysis of NGS data of small non-coding RNA." EMBnet.Journal (2012) vol. 18, pp. 100-101.
Green, et al., "Analysis of one million base pairs of Neanderthal DNA," Nature, (2006) vol. 444, pp. 330-336.
Nannya, et al, "A robust algorithm for copy number detection using high-density oligonucleotide single nucleotide polymorphism genotyping arrays," Cancer Res. (2005) vol. 65, pp. 6071-6079.
Noonan, et al., "Sequencing and Analysis of Neanderthal Genomic DNA," Science (2006) vol. 314, pp. 1113-1118.
Seo, et al., "Four-color DNA sequencing by synthesis on a chip using photocleavable fluorescent nucleotides," Proc. Nat. Acad. Sci. (2005) vol. 102, No. 17, pp. 5926-5931.
Smith, et al., "Using quality scores and longer reads improves accuracy of Solexa read mapping," BMC Bioinformatics, (2008) vol. 9, 128, pp. 1-8.
Thornley, "Analysis of Trace Data from Fluorescence Based Sanger Sequencing," (1997). Thesis, University of London Imperial College of Science, Technology and Medicine Department of Computing.
Sequenom, Inc. and Sequenom Center for Molecular Medicine LLC's Patent L.R. 3-3 Preliminary Invalidity Contentions for U.S. Patent Nos. 7,888,017, 8,008,018 and 8,195,415 and Patent L.R. 3-4 Document Production, *Verinata Health v. Sequenom*, No. 12-00865 (N. D. Cal. 2012), dated Sep. 28, 2012.
Sequenom, Inc. and Sequenom Center for Molecular Medicine LLC's Patent L. R. 4-2 Preliminary Claim Constructions and Extrinsic Evidence, *Verinata Health v. Sequenom*, No. 12-00865 (N. D. Cal. 2012), dated Oct. 26, 2012.
*Verinata Health, Inc. v. Sequenom, Inc.* Case 3:12-cv-00865-SI Document 58, pp. 1-6. Filed Nov. 21, 2012. Joint Claim Construction and Prehearing Statement Regarding Verinata Patents-in-Suit.
*Verinata Health, Inc. v. Sequenom, Inc.* Case 3:12-cv-00865-SI Document 58-1, pp. 1-47. Filed Nov. 21, 2012. Exhibit A for U.S. Patent 7,888,017 to Joint Claim Construction and Prehearing Statement.
*Verinata Health, Inc. v. Sequenom, Inc.* Case 3:12-cv-00865-SI Document 58-2, pp. 1-32. Filed Nov. 21, 2012. Exhibit B for U.S. Patent 8,008,018 to Joint Claim Construction and Prehearing Statement.
*Verinata Health, Inc. v. Sequenom, Inc.* Case 3:12-cv-00865-SI Document 58-3, pp. 1-14. Filed Nov. 21, 2012. Exhibit C for U.S. Patent 8,195,415 to Joint Claim Construction and Prehearing Statement.

*Verinata Health, Inc. v. Sequenom, Inc.* Case 3:12-cv-00865-SI Documents 60-2, pp. 5-90. Filed Nov. 21, 2012. Declaration of Dr. Michael L. Metzker Regarding Claim Construction.
*Verinata Health, Inc. v. Sequenom, Inc.* Case C-12-00865 SI, pp. 1-49. Served Nov. 21, 2012. Declaration of Stephen A. Brown, M.D. regarding claim construction of U.S. Patents 7,888,017 and 8,008,018.
Braslavsky, Ido et al.; "Sequence information can be obtained from single DNA molecules"; 2003, *PNAS*, vol. 100, No. 7, pp. 3960-3964.
Chan, K.C. Allen et al.; "Hypermethylated *RASSFIA* in Maternal Plasma: A Universal Fetal DNA Marker that Improves the Reliability of Noninvasive Prenatal Diagnosis"; 2006, *Clinical Chemistry*, vol. 52, pp. 2211-2218.
Dhallan, Ravinder et al.; "A non-invasive test for prenatal diagnosis based on fetal DNA present in maternal blood: a preliminary study"; www.thelancet.com, pp. 1-7.
Fan, H. Christina et al.; "Detection of Aneuploidy with Digital PCR"; *Department of Bioengineering, Stanford University and Howard Hughes Medical Institute*, 14 pages.
Fan, H. Christina et al.; "Noninvasive diagnosis of fetal aneuploidy by shotgun sequencing DNA from maternal blood"; 2008, Proceedings of the National Academy of Science, http://www.pnas.org/cgi/doi/10.1073/pnas.0808319105, 15 pages.
Pohl, Gudrun and Shih, Ie-Ming; "Principle and Applications of Digital PCR;" Jan. 2004; *Expert Review of Molecular Diagnostics*; vol. 4; No. 1; pp. 41-47.
Shih, Ie-Ming, et al.; "Evidence that Genetic Instability Occurs at an Early Stage of Colorectal Tumorigenesis;" Feb. 1, 2002; *Cancer Research*; vol. 61; pp. 818-822.
Office Action mailed Jun. 7, 2012 in U.S. Appl. No. 12/178,181, 9 pages.
Feinberg, Andrew, et al., "A Technique for Radiolabeling DNA Restriction Endonuclease Fragments to High Specific Activity," Analytical Biochemistry, 1983, pp. 6-13, vol. 132.
Bauer et al., Prenatal Diagnosis, 26, pp. 831-836 (2006).
Beck, Julia et al.; "Profile of the Circulating DNA in Apparently Healthy Individuals"; 2009, Clinical Chemistry, vol. 55, No. 4, pp. 730-738.
Bentley, David R.; "Whole-genome re-sequencing"; 2006, Current Opinion in Genetics & Development, vol. 16, pp. 545-552.
Bianchi, Diana, W. et al., "Large Amounts of Cell-Free DNA are Present in Amniotic Fluid," 2001, Clinical Chemistry, vol. 47, No. 10, pp. 1867-1869.
Bischoff, Fariden Z. et al.; "Cell-Free Fetal DNA and Intact Fetal Cells in Maternal Blood Circulation: Implications for First and Second Trimester Non-Invasive Prenatal Diagnosis;" Nov. 1, 2002; Human Reproduction Update; vol. 8; No. 6; pp. 493-500.
Brenner, Sydney et al.; "Gene expression analysis by massively parallel signature sequencing (MPSS) on microbead arrays"; 2000, Nature Biotechnology. vol. 18, pp. 630-634.
Campbell, Peter J. et al.; "Identification of somatically acquired rearrangements in cancer using genome-wide massively parallel paired-end sequencing"; 2008, Nature Genetics, vol. 40, No. 6, pp. 722-729.
Chan, K.C. Allen et al.; "Hypermethylated RASSF/A in Maternal Plasma: A Universal Fetal DNA Marker that Improves the Reliability of Noninvasive Prenatal Diagnosis"; 2006, Clinical Chemistry, vol. 52, pp. 2211-2218.
Chiu, Rossa, W.K. et al., "Non-Invasive Prenatal Diagnosis by Single Molecule Counting Technologies," Jul. 1, 2009, Trends in Genetics, vol. 25, No. 7, pp. 324-331.
Dear, Paul H.; "One by one: Single molecule tools for genomics"; 2003, Briefings in Functional Genomics and Proteomics, vol. 1, No. 4, pp. 397-416.
Ding, Chunming et al., "MS Analysis of Single-Nucleotide Differences in Circulating Nucleic Acids: Application to Noninvasive Prenatal Diagnosis," Jul. 20, 2004, Proceedings of the National Academy of Sciences of the United States of America, vol. 101, No. 29, pp. 10762-10767.
Emanuel et al., "Amplification of Specific Gene Products from Human Serum." GATA, Nov. 1931, 10(6):144-46.
European Examination Report Dated Jul. 13, 2010, issued in related European Application No. 08776043.5, filed Jul. 23, 2008.

(56) References Cited

OTHER PUBLICATIONS

Fan, H. Christina et al.; "Detection of Aneuploidy with Digital PCR"; Department of AB Bioengineering, Stanford University and Howard Hughes Medical Institute, submitted on May 8, 2007, 14 pages.
Fan, H. Christina et al.; "Noninvasive diagnosis of fetal aneuploidy by shotgun sequencing DNA from maternal blood"; 2008, Proceedings of the National Academy of Science, http//www.gnas.org/cgi/doi/10.1073/gnas.0808319105, 15 pages.
Farina et al., Evaluation of Cell-free Fetal DNA as a Second-Trimester Maternal Serum Marker of Down Syndrome Pregnancy, Clin.Chem., 2003, 49(2):239-42.
First Examination Report, dated Apr. 16, 2014, in Indian Patent Application 961/CHENP/2010, 2 pages.
Hahn, et al., "Prenatal Diagnosis Using Fetal Cells and Cell-Free Fetal DNA in Maternal Blood: What is Currently Feasible?" Clinical Obstetrics and Gynecology, Sep. 2002, 45(3):649-56.
Harris, Timothy D. et al.; "Single-Molecule DNA Sequencing of a Viral Genome"; 2008, Science, vol. 320, pp. 106-109.
Hearing Notice, dated Apr. 16, 2014, in Indian Patent Application 961/CHENP/2010, 2 pages.
Hromadnikova et al., Quantitative Analysis of DNA Levels ill Maternal Plasma in Normal and Down Syndrome Pregnancies, Med Central, May 2002, 1-5.
IPTAB Decision, dated Jul. 13, 2018, in Korean Patent Application No. 10-2008-7014386, 13 pages.
Judgment of Reexamination Decision, dated Aug. 30, 2018, in Chinese Patent Application No. 200880108377.1, 17 pages.
Korshunova, Yulia et al.; "Massively parallel bisulphate pyrosequencing reveals the molecular complexity of breast cancer-associated cytosine-methylation patterns obtained from tissue and serum DNA"; 2008, Genome Research, vol. 18, pp. 19-29.
Lapaire, Olav et al., "Array-CGH Analysis of Cell-Free Fetal DNA in 10 ml of Amniotic Fluid Supernatant," May 17, 2007, Prenatal Diagnosis, vol. 27, pp. 616-621.
Lapaire, Olav et al., "Cell-Free Fetal DNA in Amniotic Fluid: Unique Fragmentation Signatures in Euploid and Aneuploid Fetuses," 2007, Clinical Chemistry, vol. 53, No. 3, pp. 405-411.
Lapaire, Olav et al., "Larger Columns and Change of Lysis Buffer Increase the Yield of Cell-Free DNA Extracted from Amniotic Fluid," 2006, Letters to the Editor, Clinical Chemistry, vol. 52, No. 1, pp. 156-157.
Larabee et al., "Microarray analysis of cell-free fetal DNA in amniotic fluid: a prenatal molecular karyotype," American Journal of Human Genetics, American Society of Human Genetics, Sep. 1, 2004, pp. 485-491, vol. 75 No. 3, Chicago, IL, US.
Lecoeur, Herve, "Nuclear Apoptosis Detection by Flow Cytometry: Influence of Endogenous Endonucleases," 2002, Experimental Cell Research, vol. 277, pp. 1-14.
Li Ying et al., "Size separation of circulatory DNA in maternal plasma permits ready detection of fetal DNA polymorphisms" Clinical Chemistry, American Association for Clinical Chemistry, Jun. 1, 2004, pp. 1002-1011, vol. 50 No. 6, Washington DC.
Lo and Chiu, Nature Reviews Genetics, 8, pp. 71-77 (2007).
Lo, Y.M Dennis and Chiu, Rossa W.K.; "Prenatal Diagnosis: Progress Through Plasma Nucleic Acids," Jan. 1, 2007; Nature Reviews Genetics; vol. 8; pp. 71-77.
Lo, Y.M. Dennis et al.; "Digital PCR for the Molecular Detection of Fetal Chromosomal Aneuploidy," Aug. 7, 2007; PNAS; Vo. 104; No. 32; pp. 13116-13121.
Lo, Y.M. Dennis et al.; "Noninvasive Prenatal Diagnosis of Fetal Chromosomal Aneuploidies by Maternal Plasma Nucleic Acid Analysis;" Jan. 17, 2008; Clinical Chemistry; vol. 54; No. 3; pp. 461-466.
Lo, Y.M. Dennis et al.; "Plasma Placental RNA Allelic Ratio Permits Noninvasive Prenatal Chromosomal Aneuploidy Detection;" Feb. 2007; Nature Medicine; vol. 13, No. 2; pp. 218-223.
Lo, YMD et al. 1998 Am JHum Genet 62, 768-775.
Lun, Fiona, M. F. et al.; "Microfluidics Digital PCR Reveals a Higher Than Expected Fraction of Fetal DNA in Maternal Plasma;" Oct. 1, 2008; Clinical Chemistry; vol. 54; No. 10; pp. 1664-1672.
Lun, Fiona, M.F. et al., "Noninvasive Prenatal Diagnosis of Monogenic Diseases by Digital Size Selection and Relative Mutation Dosage on DNA in Maternal Plasma," Dec. 16, 2008, Proceedings of the National Academy of Sciences of the United States of America, vol. 105, No. 50, pp. 19920-19925.
Mann et al., Strategies for the rapid prenatal diagnosis of chromosome aneuploidy, European Journal of Human Genetics (2004), vol. 12, pp. 907-915.
Margulies, Marcel et al.; "Genome sequencing in microfabricated high-density picolitre reactors"; 2005, Nature, vol. 437, pp. 376-380.
Meyer, Matthias et al.; "From micrograms to picograms: quantitative PCR reduces the material demands of high-throughput sequencing"; 2007, Nucleic Acids Research, vol. 36, No. 1, pp. 1-6.
Notice of Final Rejection, dated Oct. 28, 2015, in Korean Patent Application No. 10-2010-7003969, 4 pages.
Notice of Results of Reconsideration, dated Apr. 14, 2016, in Korean Patent Application No. 10-2010-7003969, 2 pages.
Notification of Reexamination, dated Jun. 20, 2019, in Chinese Patent Application No. 200880108377.1, 15 pages.
Notification of Reexamination, dated Jun. 27, 2016, in Chinese Patent Application No. 200880108377.1, 3 pages.
Office Action, dated Apr. 8, 2015, in German Patent Application No. 12175754.6-1404, 10 pages.
Office Action, dated Aug. 11, 2016, in Korean Patent Application No. 10-2016-7005386, 8 pages.
Office Action, dated Aug. 28, 2014, in Korean Patent Application No. 10-2010-7003969, 3 pages.
Office Action, dated Dec. 10, 2013, in Mexican Patent Application No. MX/a/2010/000846, 3 pages.
Office Action, dated Dec. 10, 2018 in Korean Patent Application No. 10-2018-7031541, 5 pages.
Office Action, dated Dec. 21, 2018, in Chinese Patent Application No. 201710089357.5, 5 pages.
Office Action, dated Feb. 17, 2015, in Canadian Patent Application No. 2,693,081, 4 pages.
Office Action, dated Feb. 20, 2018, in Japanese Patent Application No. 2017-103772, 3 pages.
Office Action, dated Jan. 27, 2020, in Canadian Patent Application No. 3,009,992, 3 pages.
Office Action, dated Jan. 29, 2018, in Indian Patent Application No. 961/CHENP/2010, 4 pages.
Office Action, dated Jan. 30, 2014, in Canadian Patent Application No. 2,693,081, 6 pages.
Office Action, dated Jan. 31, 2018, in Eurasian Patent Application No. 201791612 (PCT/GB2008/002530), 4 pages.
Office Action, dated Jul. 2, 2013, in Japanese Patent Application No. 2010-517481, 9 pages.
Office Action, dated Jul. 23, 2019, in Japanese Patent Application No. 2018-147642, 4 pages.
Office Action, dated Jul. 3, 2019, in Chinese Patent Application No. 201710089366.4, 10 pages.
Office Action, dated Jul. 7, 2014, in Chinese Patent Application No. 200880108377.1, 9 pages.
Office Action, dated Jun. 1, 2018, in Chinese Patent Application No. 201710089366.4, 3 pages.
Office Action, dated Jun. 2, 2014, in Canadian Patent Application No. 2,693,081, 8 pages.
Office Action, dated May 2, 2012, in Australian Patent Application No. 2008278843, 2 pages.
Office Action, dated Mar. 27, 2015, in Korean Patent Application No. 10- 2010-7003969, 8 pages.
Office Action, dated Mar. 29, 2019, in Brazilian Patent Application No. PI0814670-5, 6 pages.
Office Action, dated Mar. 4, 2014, in Japanese Patent Application No. 2010-517481, 5 pages.
Office Action, dated May 15, 2020, in Chinese Patent Application No. 201710089366.4, 13 pages.
Office Action, dated May 17, 2016, in Japanese Patent Application No. 2015-085723, 5 pages.

(56) References Cited

OTHER PUBLICATIONS

Office Action, dated May 26, 2016, in Canadian Patent Application No. 2,900,927, 6 pages.
Office Action, dated Nov. 16, 2017, in Chinese Patent Application No. 201710089366.4, 3 pages.
Office Action, dated Nov. 22, 2017, in Chinese Patent Application No. 201710089357.5, 4 pages.
Office Action, dated Nov. 23, 2017, in Korean Patent Application No. 10-2017-7032673, 8 pages.
Office Action, dated Oct. 14, 2013, in German Patent Application No. 12175754.6-1404, 7 pages.
Office Action, dated Oct. 17, 2018, in Chinese Patent Application No. 201710089366.4, 7 pages.
Office Action, dated Oct. 23, 2014, in Canadian Patent Application No. 2,693,081, 10 pages.
Office Action, dated Sep. 19, 2017, in Japanese Patent Application No. 2017-103772, 7 pages.
Office Action, dated Sep. 26, 2013, in Canadian Patent Application No. 2,693,081, 3 pages.
Patent Examination Report, dated Jul. 12, 2013, in Australian Patent Application No. 2013203079, 3 pages.
PCT National Phase Rejection Decision, dated Dec. 1, 2014, in Chinese Patent Application No. 200880108377.1, 12 pages.
Peter, Inga, PhD. et al., "Cell-Free DNA Fragmentation Patters in Amniotic Fluid Identify Genetic Abnormalities and Changes due to Storage," Sep. 2008, Diagn. Mol. Pathol., vol. 17, No. 3, pp. 185-190.
Ping, Yi et al., "Use of free fetal DNA determination of pregnant female plasma in prenatal diagnosis" Chin J Obstet Gynecol, Jul. 2006, vol. 41 (7).
Pohl, Gudrun and Shih, le-Ming; "Principle and Applications of Digital PCR;" Jan. 2004; ExQert Review of Molecular Diagnostics; vol. 4; No. 1; pp. 41-47.
Reed, W. et al., "Non-Invasive Determination of the Paternal HLA Haplotype of a Fetus Using Kinetic PCR to Detect Fetal Microchimerism in Maternal Plasma," Mar. 2, 2002, Bone Marrow Transplantation, vol. 29, No. 6, pp. 527-529.
Reexamination Decision No. 116200, dated Nov. 24, 2016, in Chinese Patent Application No. 200880108377.1, 10 pages.
Reexamination Decision No. 202160, dated Feb. 13, 2020, in Chinese Patent Application No. 200880108377.1, 23 pages.
Reinartz, Jeannette et al.; "Massively parallel signature sequencing (MPSS) as a tool for in-depth quantitative gene expression profiling in all organisms"; 2002, Briefings in Functional Genomics and Proteomics, vol. 1 No. 1, pp. 95-104.
Shih, le-Ming et al.; "Evidence that Genetic Instability Occurs at an Early Stage of Colorectal Tumorigenesis;" Feb. 1, 2002; Cancer Research; vol. 61; pp. 818-822.
Soni, Gautam V. et al.; "Progress toward Ultrafast DNA Sequencing Using Solid-State Nanopores"; 2007, Clinical Chemistry, vol. 53, pp. 1996-2001.
Tettelin et al., "The nucleotide sequence of *Saccharomyces cerevisiae* chromosome VII," Nature May 29, 1997, 387:81-84.
Tong, Yu K. et al.; "Noninvasive Prenatal Detection of Fetal Trisomy 18 by Epigenetic Allelic Ratio Analysis in Maternal Plasma: Theoretical and Empirical Considerations;" Oct. 13, 2006; Clinical Chemistry; vol. 52; No. 12; pp. 2194-2202.
Tufan et al., "Analysis of Cell-Free Fetal DNA from Maternal Plasma and Serum Using a Conventional Multiplex PCR: Factors Influencing Success," Turk J Med Sci, Nov. 19, 2004, 35:85-92.
Wapner et al., "First-Trimester Screening for Trisomies 21 and 18," The New England Journal of Medicine, 2003, vol. 349, No. 15, c. 1405-1413.
Wheeler, David A. et al., "The complete genome of an individual by massively parallel DNA sequencing," 2008, Nature, vol. 452, pp. 872-877.
Zhong, Xiao Yan et al.; "Fetal DNA in Maternal Plasma is Elevated in Pregnancies with Aneuploid Fetuses;" Oct. 1, 2000; Prenatal Diagnosis; vol. 20; No. 10; pp. 795-798.
Zhou, Wei et al., "Counting Alleles to Predict Recurrence of Early-Stage Colorectal Cancers," Jan. 19, 2002; The Lancet; vol. 359; No. 9302; pp. 219-225.
Office Action, dated May 15, 2020, in Eurasian Patent Application No. 201791612 (PCT/GB2008/002530), 2 pages.
Office Action, dated May 6, 2020, in Chinese Patent Application No. 201710198531.X, 13 pages.
Notice of Invalidation Trial Request No. 7-7-2023-000575334, dated Jan. 30, 2023, in Korean Patent Application No. 10-2112438, 4 pages.
Notice of Invalidation Trial Request No. 7-7-2023-0006+9593, dated Jan. 30, 2023, in Korean Patent Application No. 10-2147626, 2 pages.
Reexamination Decision No. 202160, dated Aug. 14, 2022, in Chinese Patent Application No. 200880108377.1, 27 pages.
Hilditch C.J and Rustovitz D., "Normalization of Chromosome Measurements," Comput. Bio. Med., 1972, 2:167-179, 13 pages.
Jorgez C et al., "Elevated levels of total (maternal and fetal) beta-globin DNA in maternal blood from first trimester pregnancies with trisomy 21," Human Reproduction, Jun. 21, 2007, 8:2267-2272, 6 pages.
Nuss S et al., "Maternal cell contamination in amniotic fluid samples as a consequence of the sampling technique," Human Genetics, 1994, 93:121-124.
Mouatassim S. E. et al., "Prenatal diagnosis of common aneuploidies using multiplex quantitative fluorescent polymerase chain reaction," Fetal Diagn Ther., 2004, 19:496-503.
Porreca G. J. et al., "Multiplex amplification of large sets of human exons," Nature Methods, Oct. 14, 2007, 4:931-936.
Binladen J et al., "The use of coded PCR primers enables high-throughput sequencing of multiple homolog amplification products by 454 parallel sequencing," PLoS One, Feb. 2007, 2:e197, 9 pages.
Berka J et al., "Genome sequencer 20 system: breakthrough in a new applications age of sequencing," DNA Sequencing, 2006, 4:7-10.
Sterky F and J. Lundeberg, "Sequence analysis of genes and genomes," Journal of Biotechnology, 2000, 76:1-31.
Yamada T et al., "PrimerStation: a highly specific multiplex genomic PCR primer design server for the human genome," Nucleic Acids Research, 2006, 34:W665-W669.
Thomas R. K. et al., "Sensitive mutation detection in heterogeneous cancer specimens by massively parallel picoliter reactor sequencing," Nature Medicine, Jul. 2006, 12(7):852-855.
Tsang J. C. et al., "Circulating nucleic acids in plasma/serum," Pathology, Apr. 2007, 39(2):197-207.
Zhong X. Y. et al., "Cell-free foetal DNA in maternal plasma does not appear to be derived from the rich pool of cell-free foetal DNA in amniotic fluid," Archives of Gynecology and Obstetrics, Jan. 2006, 273(4):221-226.
European Opposition Decision for Patent Application No. 08776043.5, dated Jul. 18, 2016, 18 pages.
European Appeal Decision in Patent Application No. 08776043.5, dated Sep. 12, 2017, 43 pages.
European Opposition Decision for Patent Application No. 12175754.6, dated Dec. 12, 2018, 29 pages.

* cited by examiner

| Sample | Total no. of sequenced tags | Total no. of sequenced basepairs | Proportion of the human genome (%) | U0 count | U0 count / total count (%) | No. of U0 sequenced basepairs | U0 Proportion of the human genome (%) |
|---|---|---|---|---|---|---|---|
| Sample 1 T21 | 1.12E+07 | 4.02E+08 | 13.4 | 1.93E+06 | 17.3 | 6.94E+07 | 2.31 |
| Sample 2 T21 | 1.04E+07 | 3.73E+08 | 12.4 | 1.80E+06 | 17.4 | 6.50E+07 | 2.17 |
| Sample 3 T21 | 8.90E+06 | 3.20E+08 | 10.7 | 2.09E+06 | 23.4 | 7.51E+07 | 2.50 |
| Sample 4 T21 | 1.02E+07 | 3.69E+08 | 12.3 | 2.23E+06 | 21.7 | 8.02E+07 | 2.67 |
| Sample 5 euploid | 1.06E+07 | 3.83E+08 | 12.8 | 2.12E+06 | 19.9 | 7.62E+07 | 2.54 |
| Sample 6 euploid | 9.58E+06 | 3.45E+08 | 11.5 | 1.91E+06 | 20.0 | 6.88E+07 | 2.29 |
| Sample 7 euploid | 9.55E+06 | 3.44E+08 | 11.5 | 2.01E+06 | 21.0 | 7.22E+07 | 2.41 |
| Sample 8 euploid | 9.09E+06 | 3.27E+08 | 10.9 | 2.09E+06 | 23.0 | 7.53E+07 | 2.51 |

FIG. 6

| No. of sequences in each subset | Euploid | | | | T21 (5%) | | | | Successful Differentiation (vs euploid)? |
|---|---|---|---|---|---|---|---|---|---|
| | Mean | SD | 5 percentile | 95 percentile | Mean | 5 percentile | 95 percentile | | |
| 60,000 | 1.322% | 0.036% | 1.250% | 1.395% | 1.355% | 1.283% | 1.428% | | *No* |
| 120,000 | 1.322% | 0.022% | 1.277% | 1.367% | 1.355% | 1.311% | 1.400% | | *No* |
| 180,000 | 1.322% | 0.016% | 1.291% | 1.353% | 1.355% | 1.324% | 1.386% | | *No* |
| 240,000 | 1.322% | 0.013% | 1.295% | 1.349% | 1.355% | 1.328% | 1.382% | | *No* |
| 300,000 | 1.322% | 0.011% | 1.301% | 1.344% | 1.355% | 1.334% | 1.377% | | *No* |
| 360,000 | 1.322% | 0.010% | 1.302% | 1.343% | 1.355% | 1.335% | 1.376% | | *No* |
| 420,000 | 1.322% | 0.095% | 1.303% | 1.341% | 1.355% | 1.336% | 1.374% | | *No* |
| 480,000 | 1.322% | 0.009% | 1.305% | 1.339% | 1.355% | 1.338% | 1.372% | | *No* |
| 540,000 | 1.322% | 0.008% | 1.306% | 1.339% | 1.355% | 1.339% | 1.372% | | *Yes* |

*Fig 7A*

| No. of sequences in each subset | T21 (10%) | | | | T21 (20%) | | | |
|---|---|---|---|---|---|---|---|---|
| | Mean | 5 percentile | 95 percentile | Successful Differentiation (vs euploid)? | Mean | 5 percentile | 95 percentile | Successful Differentiation (vs euploid)? |
| 60,000 | 1.388% | 1.316% | 1.461% | No | 1.454% | 1.382% | 1.527% | No |
| 120,000 | 1.388% | 1.344% | 1.433% | No | 1.454% | 1.410% | 1.499% | Yes |
| 180,000 | 1.388% | 1.357% | 1.420% | Yes | 1.454% | 1.423% | 1.486% | Yes |
| 240,000 | 1.388% | 1.361% | 1.415% | Yes | 1.454% | 1.427% | 1.481% | Yes |
| 300,000 | 1.388% | 1.367% | 1.410% | Yes | 1.454% | 1.433% | 1.476% | Yes |
| 360,000 | 1.388% | 1.368% | 1.409% | Yes | 1.454% | 1.434% | 1.475% | Yes |
| 420,000 | 1.388% | 1.369% | 1.407% | Yes | 1.454% | 1.435% | 1.473% | Yes |
| 480,000 | 1.388% | 1.371% | 1.405% | Yes | 1.454% | 1.437% | 1.471% | Yes |
| 540,000 | 1.388% | 1.372% | 1.405% | Yes | 1.454% | 1.438% | 1.471% | Yes |

Fig. 7B

| Sequenced tag order | Sample 1 T21 | Sample 2 T21 | Sample 3 T21 | Sample 4 T21 | Sample 5 Euploid | Sample 6 Euploid | Sample 7 Euploid | Sample 8 Euploid |
|---|---|---|---|---|---|---|---|---|
| 1 | 9796394 | 9798087 | 9798123 | 9795700 | 9797841 | 9795972 | 9796536 | 9795601 |
| 2 | 9797424 | 9798402 | 9798250 | 9797860 | 9798176 | 9796549 | 9796863 | 9797404 |
| 3 | 9797438 | 9798708 | 9798715 | 9797864 | 9798835 | 9797359 | 9798161 | 9798117 |
| 4 | 9798112 | 9799733 | 9799467 | 9798106 | 9800315 | 9797418 | 9798401 | 9798175 |
| 5 | 9798394 | 9799852 | 9799730 | 9799209 | 9800385 | 9797446 | 9798722 | 9798387 |
| 6 | 9798729 | 9800362 | 9799788 | 9799440 | 9800554 | 9797860 | 9799752 | 9798816 |
| 7 | 9798768 | 9800914 | 9799834 | 9799440 | 9800820 | 9798062 | 9800317 | 9799732 |
| 8 | 9798816 | 9801528 | 9800332 | 9799741 | 9800829 | 9798135 | 9800800 | 9800144 |
| 9 | 9799421 | 9801779 | 9800869 | 9799812 | 9800832 | 9798707 | 9801380 | 9800421 |
| 10 | 9799464 | 9803801 | 9800881 | 9799833 | 9800866 | 9798715 | 9801699 | 9800827 |

FIG. 8A

| Sequenced tag order | Sample 1 T21 | Sample 2 T21 | Sample 3 T21 | Sample 4 T21 | Sample 5 Euploid | Sample 6 Euploid | Sample 7 Euploid | Sample 8 Euploid |
|---|---|---|---|---|---|---|---|---|
| 1 | 14469232 | 14510976 | 14510792 | 14510867 | 14434681 | 14510711 | 14512069 | 14510996 |
| 2 | 14503781 | 14511307 | 14510807 | 14511312 | 14506660 | 14510835 | 14512407 | 14522947 |
| 3 | 14510805 | 14511512 | 14510886 | 14511983 | 14511219 | 14511308 | 14522879 | 14530478 |
| 4 | 14510824 | 14511755 | 14511816 | 14522914 | 14511328 | 14511354 | 14609732 | 14565255 |
| 5 | 14510965 | 14511774 | 14512410 | 14522978 | 14511377 | 14511703 | 14628248 | 14609733 |
| 6 | 14511369 | 14512067 | 14522944 | 14523028 | 14511432 | 14511703 | 14675246 | 14628261 |
| 7 | 14511702 | 14512190 | 14523047 | 14565245 | 14511597 | 14512184 | 14675250 | 14668784 |
| 8 | 14511738 | 14522891 | 14564769 | 14628257 | 14511755 | 14512204 | 14680184 | 14680163 |
| 9 | 14523000 | 14539630 | 14565205 | 14635374 | 14512204 | 14524806 | 14692539 | 14689547 |
| 10 | 14524823 | 14541260 | 14565251 | 14665101 | 14512204 | 14565230 | 14694114 | 14689592 |

FIG. 8B

| Case No. | Gestational age (weeks + days) | Karyotype | Plasma Volume (mL) | Input DNA (ng)[a] | Fetal percentage (%)[b] | Total sequence count[c] | Sorted counts of read1[d] | Sorted counts of read2[d] | Sorted U0-1-0-0 counts of read1[e] (% of total) | Paired reads[f] | Accepted PE reads (% of total) |
|---|---|---|---|---|---|---|---|---|---|---|---|
| 6 | 12 + 5 | 46XY | 4.8 | 4.1 | 7.2 | 9 517 549 | 2 561 774 | 2 230 316 | 1 850 429 (19.4%) | 1 671 425 | 1 002 834 (10.5%) |
| 7 | 13 + 5 | 46XY | 4.8 | 6.1 | 7.9 | 9 593 914 | 3 684 793 | 3 491 151 | 2 697 877 (28.1%) | 2 603 845 | 1 734 737 (18.1%) |
| 8 | 12 + 6 | 46XY | 4.8 | 13.0 | 2.6 | 9 945 029 | 3 776 056 | 3 578 640 | 2 760 386 (27.8%) | 2 686 091 | 1 786 242 (18.0%) |
| 4467 | 14 + 4 | 47XY +21 | 4.0 | 4.3 | 16.2 | 10 368 770 | 3 602 352 | 3 388 313 | 2 615 616 (25.2%) | 2 559 014 | 1 686 055 (16.3%) |
| 4620 | 12 + 4 | 47XY +21 | 5.6 | 6.3 | 8.8 | 9 628 874 | 3 771 381 | 3 589 798 | 2 758 156 (28.6%) | 2 683 235 | 1 806 950 (18.8%) |
| 9 | 17 + 2 | 46XX | 4.8 | 6.6 | n/a | 9 777 804 | 3 634 731 | 3 427 930 | 2 653 199 (27.1%) | 2 558 772 | 1 681 648 (17.2%) |
| 10 | 17 + 1 | 46XX | 4.8 | 5.2 | n/a | 9 511 784 | 3 428 613 | 3 259 349 | 2 505 064 (26.3%) | 2 444 362 | 1 618 291 (17.0%) |
| 16 | 12 + 4 | 46XX | 4.8 | 6.7 | n/a | 8 878 573 | 3 215 146 | 3 043 879 | 2 216 696 (25.0%) | 2 295 192 | 1 341 424 (15.1%) |
| 22 | 13 + 6 | 46XX | 4.8 | 3.2 | 5.3 | 10 041 629 | 3 507 741 | 2 960 587 | 2 531 538 (25.2%) | 2 236 283 | 1 329 515 (13.2%) |
| 12 | 13 | 46XY | 4.8 | 10.3 | 3.2 | 8 768 612 | 3 371 715 | 3 026 776 | 2 394 173 (27.3%) | 2 260 935 | 1 364 798 (15.6%) |
| 20 | 13 + 3 | 46XY | 4.8 | 7.1 | 5.7 | 8 319 431 | 3 155 943 | 2 958 106 | 2 240 088 (26.9%) | 2 219 550 | 1 430 068 (17.2%) |
| 2849 | 14 + 3 | 47XY +21 | 4.0 | 5.9 | 2.2 | 10 104 453 | 3 344 533 | 3 164 141 | 2 414 339 (23.9%) | 2 376 096 | 1 570 738 (15.5%) |
| 4386 | 13 + 6 | 47XY +21 | 3.0 | 12.6 | | 10 533 749 | 3 870 157 | 3 699 576 | 2 777 640 (26.4%) | 2 775 839 | 1 837 304 (17.4%) |

[a] A conversion factor of 6.6 pg of DNA per genome equivalent as detected by the readouts of the *HBB* real-time PCR assay was used to calculate the yield of extracted plasma DNA.
[b] The fetal DNA percentage was calculated by the readouts of the *HBB* and *SRY* real-time PCR.
[c] The total number of detected clusters per sample. Each cluster was derived from solid phase 'bridge' amplification from a single DNA molecule. The two ends of each DNA molecule were sequenced.
[d] Sequenced reads that could be aligned to one location in the repeat-masked reference human genome.
[e] Reads that were aligned to one location in the human genome with no mismatches to the repeat-masked reference human genome.
[f] Pairs of sorted read1 and read2 that were sequenced on the same physical cluster position.

FIG. 13

DIAGNOSING FETAL CHROMOSOMAL ANEUPLOIDY USING GENOMIC SEQUENCING

CLAIM OF PRIORITY

This application claims priority to and is a continuation-in-part application of U.S. application Ser. No. 12/178,181, entitled "DIAGNOSING FETAL CHROMOSOMAL ANEUPLOIDY USING MASSIVELY PARALLEL GENOMIC SEQUENCING" filed Jul. 23, 2008, which claims priority from U.S. Provisional Application No. 60/951,438, entitled "DETERMINING A NUCLEIC ACID SEQUENCE IMBALANCE" filed Jul. 23, 2007, the entire contents of which are herein incorporated by reference for all purposes.

FIELD OF THE INVENTION

This invention generally relates to the diagnostic testing of fetal chromosomal aneuploidy by determining imbalances between different nucleic acid sequences, and more particularly to the identification of trisomy 21 (Down syndrome) and other chromosomal aneuploidies via testing a maternal sample (e.g. blood).

BACKGROUND

Fetal chromosomal aneuploidy results from the presence of abnormal dose(s) of a chromosome or chromosomal region. The abnormal dose(s) can be abnormally high, e.g. the presence of an extra chromosome 21 or chromosomal region in trisomy 21; or abnormally low, e.g. the absence of a copy of chromosome X in Turner syndrome.

Conventional prenatal diagnostic methods of a fetal chromosomal aneuploidy, e.g., trisomy 21, involve the sampling of fetal materials by invasive procedures such as amniocentesis or chorionic villus sampling, which pose a finite risk of fetal loss. Non-invasive procedures, such as screening by ultrasonography and biochemical markers, have been used to risk-stratify pregnant women prior to definitive invasive diagnostic procedures. However, these screening methods typically measure epiphenomena that are associated with the chromosomal aneuploidy, e.g., trisomy 21, instead of the core chromosomal abnormality, and thus have suboptimal diagnostic accuracy and other disadvantages, such as being highly influenced by gestational age.

The discovery of circulating cell-free fetal DNA in maternal plasma in 1997 offered new possibilities for noninvasive prenatal diagnosis (Lo, Y M D and Chiu, R W K 2007 Nat Rev Genet 8, 71-77). While this method has been readily applied to the prenatal diagnosis of sex-linked (Costa, J M et al. 2002 N Engl J Med 346, 1502) and certain single gene disorders (Lo, Y M D et al. 1998 N Engl J Med 339, 1734-1738), its application to the prenatal detection of fetal chromosomal aneuploidies has represented a considerable challenge (Lo, Y M D and Chiu, R W K 2007, supra). First, fetal nucleic acids co-exist in maternal plasma with a high background of nucleic acids of maternal origin that can often interfere with the analysis of fetal nucleic acids (Lo, Y M D et al. 1998 Am J Hum Genet 62, 768-775). Second, fetal nucleic acids circulate in maternal plasma predominantly in a cell-free form, making it difficult to derive dosage information of genes or chromosomes within the fetal genome.

Significant developments overcoming these challenges have recently been made (Benachi, A & Costa, J M 2007 Lancet 369, 440-442). One approach detects fetal-specific nucleic acids in the maternal plasma, thus overcoming the problem of maternal background interference (Lo, Y M D and Chiu, R W K 2007, supra). Dosage of chromosome 21 was inferred from the ratios of polymorphic alleles in the placenta-derived DNA/RNA molecules. However, this method is less accurate when samples contain lower amount of the targeted nucleic acid and can only be applied to fetuses who are heterozygous for the targeted polymorphisms, which is only a subset of the population if one polymorphism is used.

Dhallan et al (Dhallan, R, et al. 2007, supra Dhallan, R, et al. 2007 Lancet 369, 474-481) described an alternative strategy of enriching the proportion of circulating fetal DNA by adding formaldehyde to maternal plasma. The proportion of chromosome 21 sequences contributed by the fetus in maternal plasma was determined by assessing the ratio of paternally-inherited fetal-specific alleles to non-fetal-specific alleles for single nucleotide polymorphisms (SNPs) on chromosome 21. SNP ratios were similarly computed for a reference chromosome. An imbalance of fetal chromosome 21 was then inferred by detecting a statistically significant difference between the SNP ratios for chromosome 21 and those of the reference chromosome, where significant is defined using a fixed p-value of <0.05. To ensure high population coverage, more than 500 SNPs were targeted per chromosome. However, there have been controversies regarding the effectiveness of formaldehyde to enrich fetal DNA to a high proportion (Chung, G T Y, et al. 2005 Clin Chem 51, 655-658), and thus the reproducibility of the method needs to be further evaluated. Also, as each fetus and mother would be informative for a different number of SNPs for each chromosome, the power of the statistical test for SNP ratio comparison would be variable from case to case (Lo, Y M D & Chiu, R W K. 2007 Lancet 369, 1997). Furthermore, since these approaches depend on the detection of genetic polymorphisms, they are limited to fetuses heterozygous for these polymorphisms.

Using polymerase chain reaction (PCR) and DNA quantification of a chromosome 21 locus and a reference locus in amniocyte cultures obtained from trisomy 21 and euploid fetuses, Zimmermann et al (2002 Clin Chem 48, 362-363) were able to distinguish the two groups of fetuses based on the 1.5-fold increase in chromosome 21 DNA sequences in the former. Since a 2-fold difference in DNA template concentration constitutes a difference of only one threshold cycle (Ct), the discrimination of a 1.5-fold difference has been the limit of conventional real-time PCR. To achieve finer degrees of quantitative discrimination, alternative strategies are needed.

Digital PCR has been developed for the detection of allelic ratio skewing in nucleic acid samples (Chang, H W et al. 2002 J Natl Cancer Inst 94, 1697-1703). Digital PCR is an amplification based nucleic acid analysis technique which requires the distribution of a specimen containing nucleic acids into a multitude of discrete samples where each sample containing on average not more than about one target sequence per sample. Specific nucleic acid targets are amplified with sequence-specific primers to generate specific amplicons by digital PCR. The nucleic acid loci to be targeted and the species of or panel of sequence-specific primers to be included in the reactions are determined or selected prior to nucleic acid analysis.

Clinically, it has been shown to be useful for the detection of loss of heterozygosity (LOH) in tumor DNA samples (Zhou, W. et al. 2002 Lancet 359, 219-225). For the analysis of digital PCR results, sequential probability ratio testing (SPRT) has been adopted by previous studies to classify the experimental results as being suggestive of the presence of LOH in a sample or not (El Karoui at al. 2006 Stat Med 25, 3124-3133).

In methods used in the previous studies, the amount of data collected from the digital PCR is quite low. Thus, the accuracy can be compromised due to the small number of data points and typical statistical fluctuations.

It is therefore desirable that noninvasive tests have high sensitivity and specificity to minimize false negatives and false positives, respectively. However, fetal DNA is present in low absolute concentration and represent a minor portion of all DNA sequences in maternal plasma and serum. It is therefore also desirable to have methods that allow the noninvasive detection of fetal chromosomal aneuploidy by maximizing the amount of genetic information that could be inferred from the limited amount of fetal nucleic acids which exist as a minor population in a biological sample containing maternal background nucleic acids.

BRIEF SUMMARY

Embodiments of this invention provide methods, systems, and apparatus for determining whether a nucleic acid sequence imbalance (e.g., chromosome imbalance) exists within a biological sample obtained from a pregnant female. This determination may be done by using a parameter of an amount of a clinically-relevant chromosomal region in relation to other non-clinically-relevant chromosomal regions (background regions) within a biological sample. In one aspect, an amount of chromosomes is determined from a sequencing of nucleic acid molecules in a maternal sample, such as urine, plasma, serum, and other suitable biological samples. Nucleic acid molecules of the biological sample are sequenced, such that a fraction of the genome is sequenced. One or more cutoff values are chosen for determining whether a change compared to a reference quantity exists (i.e. an imbalance), for example, with regards to the ratio of amounts of two chromosomal regions (or sets of regions). The sensitivity of the change compared to a reference quantity is increased by enriching the amount of fetal sequences being counted relative to the amount of maternal sequences being counted. Thus, changes compared to the reference quantity can be more pronounced and accurate. In one aspect, such enrichment is balanced with a need to have a sufficient number of sequences with which to perform the analysis.

According to one exemplary embodiment, a biological sample received from a pregnant female is analyzed to perform a prenatal diagnosis of a fetal chromosomal aneuploidy. The biological sample includes nucleic acid molecules. A portion of the nucleic acid molecules contained in the biological sample are sequenced. Both ends of respective nucleic acids are sequenced in order to provide a length of each sequence. For example, a comparison of both ends to a reference sequence (e.g. the entire genome) may be used to provide the length.

Based on the sequencing, a first amount of a first chromosome is determined from sequences identified as originating from the first chromosome. A second amount of one or more second chromosomes is determined from sequences identified as originating from one of the second chromosomes. The counting of the first and second amounts is dependent on the lengths of the sequences that are counted. A higher relative count of sequences from the fetus can thus be provided since the proportion of sequences that are maternal relative to fetal is also length dependent.

Further, a parameter from the first amount and the second amount is then compared to one or more cutoff values. Based on the comparison, a classification of whether a fetal chromosomal aneuploidy exists for the first chromosome is determined.

According to another exemplary embodiment, a biological sample received from a pregnant female is analyzed to perform a prenatal diagnosis of a fetal chromosomal aneuploidy. The biological sample includes nucleic acid molecules and has been enriched for sequences less than a first predetermined number of nucleotides, where the first predetermined number is between about 125 and about 175 nucleotides.

Based on the sequencing, a first amount of a first chromosome is determined from sequences identified as originating from the first chromosome. A second amount of one or more second chromosomes is determined from sequences identified as originating from one of the second chromosomes. A parameter from the first amount and the second amount is then compared to one or more cutoff values. Based on the comparison, a classification of whether a fetal chromosomal aneuploidy exists for the first chromosome is determined. The enrichment advantageously provides a higher relative count of sequences from the fetus to provide greater ease in determining an aneuploidy while still maintaining a sufficient number of total sequences to prevent errors, such as false positives.

Other embodiments of the invention are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 6 shows a table of a portion of human genome that was analyzed according to an embodiment of the present invention. T21 denote a sample obtained from a pregnancy involving a trisomy 21 fetus.

FIGS. 7A and 7B show a table of a number of sequences required to differentiate euploid from trisomy 21 fetuses according to an embodiment of the present invention.

FIG. 8A shows a table of top ten starting positions of sequenced tags aligned to chromosome 21 according to an embodiment of the present invention.

FIG. 8B shows a table of top ten starting positions of sequenced tags aligned to chromosome 22 according to an embodiment of the present invention.

FIG. 13 shows a table of a summary of clinical information and sequence counts for the first and second trimester pregnancies studied according to an embodiment of the present invention.

DEFINITIONS

Figure 1A:
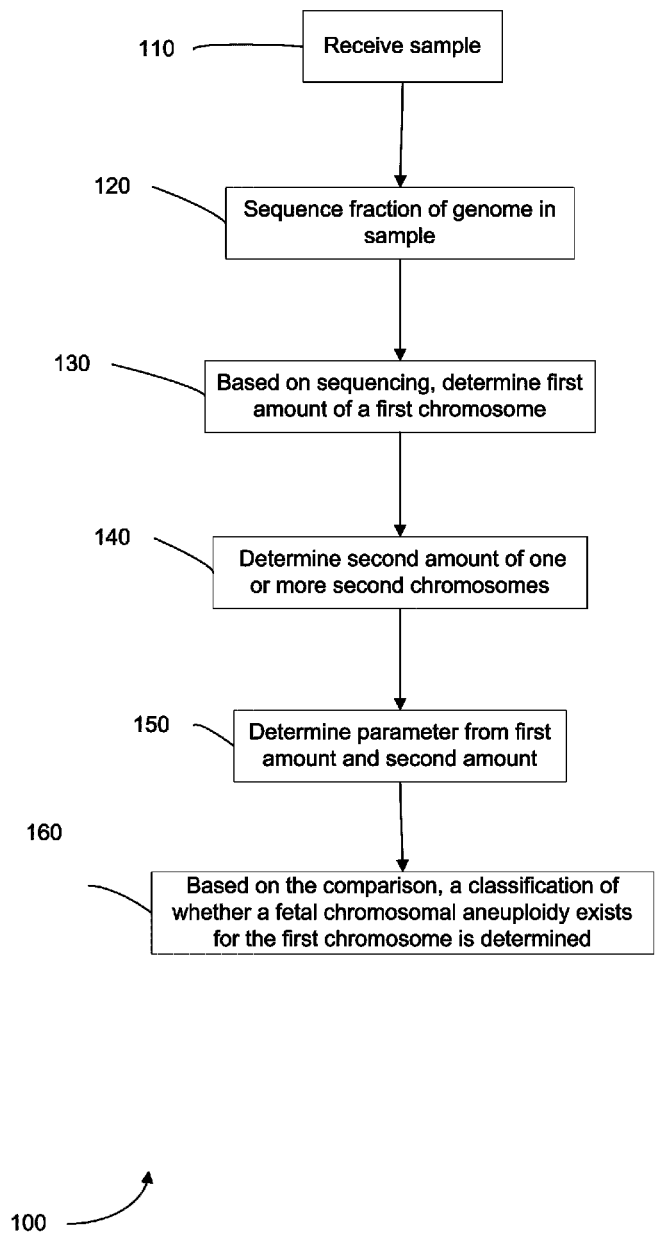
FIG. 1A is a flowchart of a method 100 for performing prenatal diagnosis of a fetal chromosomal aneuploidy in a biological sample obtained from a pregnant female subject according to an embodiment of the present invention.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain. It may include regions preceding and following the coding region (leader and trailer) as well as intervening sequences (introns) between individual coding segments (exons).

The term "reaction" as used herein refers to any process involving a chemical, enzymatic, or physical action that is indicative of the presence or absence of a particular polynucleotide sequence of interest. An example of a "reaction" is an amplification reaction such as a polymerase chain reaction (PCR). Another example of a "reaction" is a sequencing reaction, either by synthesis or by ligation. An "informative reaction" is one that indicates the presence of one or more particular polynucleotide sequence of interest, and in one case where only one sequence of interest is present. The term "well" as used herein refers to a reaction at a predetermined location within a confined structure, e.g., a well-shaped vial, cell, or chamber in a PCR array.

The term "clinically relevant nucleic acid sequence" as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents. Yet other examples include sequences which are mutated, deleted, or amplified in a malignant tumor, e.g. sequences in which loss of heterozygosity or gene duplication occur. In some embodiments, multiple clinically relevant nucleic acid sequences, or equivalently multiple makers of the clinically relevant nucleic acid sequence, can be used to provide data for detecting the imbalance. For instance, data from five non-consecutive sequences on chromosome 21 can be used in an additive fashion for the determination of possible chromosomal 21 imbalance, effectively reducing the need of sample volume to ⅕.

The term "background nucleic acid sequence" as used herein may refer to nucleic acid sequences originating from the mother or originating from a chromosome not tested for aneuploidy in a particular analysis, which can be, e.g., a bioinformatic one, or one involving laboratory work, or a combination.

The term "reference nucleic acid sequence" as used herein refers to a nucleic acid sequence whose average concentration per reaction is known or equivalently has been measured.

The term "overrepresented nucleic acid sequence" as used herein refers to the nucleic acid sequence among two sequences of interest (e.g., a clinically relevant sequence and a background sequence) that is in more abundance than the other sequence in a biological sample.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "quantitative data" as used herein means data that are obtained from one or more reactions and that provide one or more numerical values. For example, the number of wells that show a fluorescent marker for a particular sequence would be quantitative data.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

The term "cutoff value" as used herein means a numerical value whose value is used to arbitrate between two or more states (e.g. diseased and non-diseased) of classification for a biological sample. For example, if a parameter is greater than the cutoff value, a first classification of the quantitative data is made (e.g. diseased state); or if the parameter is less than the cutoff value, a different classification of the quantitative data is made (e.g. non-diseased state).

The term "imbalance" as used herein means any significant deviation as defined by at least one cutoff value in a quantity of the clinically relevant nucleic acid sequence from a reference quantity. For example, the reference quantity could be a ratio of 3/5, and thus an imbalance would occur if the measured ratio is 1:1.

The term "chromosomal aneuploidy" as used herein means a variation in the quantitative amount of a chromosome from that of a diploid genome. The variation may be a gain or a loss. It may involve the whole of one chromosome or a region of a chromosome.

The term "random sequencing" as used herein refers to sequencing whereby the nucleic acid fragments sequenced have not been specifically identified or targeted before the sequencing procedure. Sequence-specific primers to target specific gene loci are not required. The pools of nucleic acids sequenced vary from sample to sample and even from analysis to analysis for the same sample. The identities of the sequenced nucleic acids are only revealed from the sequencing output generated. In some embodiments of the present invention, the random sequencing may be preceded by procedures to enrich a biological sample with particular populations of nucleic acid molecules sharing certain common features. In one embodiment, each of the fragments in the biological sample have an equal probability of being sequenced.

The term "fraction of the human genome" or "portion of the human genome" as used herein refers to less than 100% of the nucleotide sequences in the human genome which comprises of some 3 billion basepairs of nucleotides. In the context of sequencing, it refers to less than 1-fold coverage of the total nucleotide sequences in the human genome. The term may be expressed as a percentage or absolute number of nucleotides/basepairs. As an example of use, the term may be used to refer to the actual amount of sequencing performed. Embodiments may determine the required minimal value for the sequenced fraction of the human genome to obtain an accurate diagnosis. As another example of use, the term may refer to the amount of sequenced data used for deriving a parameter or amount for disease classification.

The term "sequenced tag" as used herein refers to string of nucleotides sequenced from any part or all of a nucleic acid molecule. For example, a sequenced tag may be a short string of nucleotides sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

DETAILED DESCRIPTION

Embodiments of this invention provide methods, systems, and apparatus for determining whether an increase or decrease (diseased state) of a clinically-relevant chromosomal region exists compared to a non-diseased state. This determination may be done by using a parameter of an amount of a clinically-relevant chromosomal region in relation to other non-clinically-relevant chromosomal regions (background regions) within a biological sample. Nucleic acid molecules of the biological sample are sequenced, such that a fraction of the genome is sequenced, and the amount may be determined from results of the sequencing. One or more cutoff values are chosen for determining whether a change compared to a reference quantity exists (i.e. an imbalance), for example, with regards to the ratio of amounts of two chromosomal regions (or sets of regions).

The change detected in the reference quantity may be any deviation (upwards or downwards) in the relation of the clinically-relevant nucleic acid sequence to the other non-clinically-relevant sequences. Thus, the reference state may be any ratio or other quantity (e.g. other than a 1-1 correspondence), and a measured state signifying a change may be any ratio or other quantity that differs from the reference quantity as determined by the one or more cutoff values.

The clinically relevant chromosomal region (also called a clinically relevant nucleic acid sequence) and the background nucleic acid sequence may come from a first type of cells and from one or more second types of cells. For example, fetal nucleic acid sequences originating from fetal/placental cells are present in a biological sample, such as maternal plasma, which contains a background of maternal nucleic acid sequences originating from maternal cells. In one embodiment, the cutoff value is determined based at least in part on a percentage of the first type of cells in a biological sample. Note the percentage of fetal sequences in a sample may be determined by any fetal-derived loci and not limited to measuring the clinically-relevant nucleic acid sequences. In another embodiment, the cutoff value is determined at least in part on the percentage of tumor sequences in a biological sample, such as plasma, serum, saliva or urine, which contains a background of nucleic acid sequences derived from the non-malignant cells within the body.

I. General Method

FIG. 1A is a flowchart of a method 100 for performing prenatal diagnosis of a fetal chromosomal aneuploidy in a biological sample obtained from a pregnant female subject according to an embodiment of the present invention.

In step 110, a biological sample from the pregnant female is received. The biological sample may be plasma, urine, serum, or any other suitable sample. The sample contains nucleic acid molecules from the fetus and the pregnant female. For example, the nucleic acid molecules may be fragments from chromosomes.

In step 120, at least a portion of a plurality of the nucleic acid molecules contained in the biological sample are sequenced. The portion sequenced represents a fraction of the human genome. In one embodiment, the nucleic acid molecules are fragments of respective chromosomes. One end (e.g. 35 basepairs (bp)), both ends, or the entire fragment may be sequenced. All of the nucleic acid molecules in the sample may be sequenced, or just a subset may be sequenced. This subset may be randomly chosen, as will be described in more detail later.

In one embodiment, the sequencing is done using massively parallel sequencing. Massively parallel sequencing, such as that achievable on the 454 platform (Roche) (Margulies, M. et al. 2005 Nature 437, 376-380), Illumina Genome Analyzer (or Solexa platform) or SOLiD System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001), allow the sequencing of many nucleic acid molecules isolated from a specimen at high orders of multiplexing in a parallel fashion (Dear Brief Funct Genomic Proteomic 2003; 1: 397-416). Each of these platforms sequences clonally expanded or even non-amplified single molecules of nucleic acid fragments.

As a high number of sequencing reads, in the order of hundred thousands to millions or even possibly hundreds of millions or billions, are generated from each sample in each run, the resultant sequenced reads form a representative profile of the mix of nucleic acid species in the original specimen. For example, the haplotype, trascriptome and methylation profiles of the sequenced reads resemble those of the original specimen (Brenner et al Nat Biotech 2000; 18: 630-634; Taylor et al Cancer Res 2007; 67: 8511-8518). Due to the large sampling of sequences from each specimen, the number of identical sequences, such as that generated from the sequencing of a nucleic acid pool at several folds of coverage or high redundancy, is also a good quantitative representation of the count of a particular nucleic acid species or locus in the original sample.

In step 130, based on the sequencing (e.g. data from the sequencing), a first amount of a first chromosome (e.g. the clinically relevant chromosome) is determined. The first amount is determined from sequences identified as originating from the first chromosome. For example, a bioinformatics procedure may then be used to locate each of these DNA sequences to the human genome. It is possible that a proportion of such sequences will be discarded from subsequent analysis because they are present in the repeat regions of the human genome, or in regions subjected to inter-individual variations, e.g. copy number variations. An amount of the chromosome of interest and of one or more other chromosomes may thus be determined.

In step 140, based on the sequencing, a second amount of one or more second chromosomes is determined from sequences identified as originating from one of the second chromosomes. In one embodiment, the second chromosomes are all of the other chromosomes besides the first one (i.e. the one being tested). In another embodiment, the second chromosome is just a single other chromosome.

There are a number of ways of determining the amounts of the chromosomes, including but not limited to counting the number of sequenced tags, the number of sequenced nucleotides (basepairs) or the accumulated lengths of sequenced nucleotides (basepairs) originating from particular chromosome(s) or chromosomal regions.

In another embodiment, rules may be imposed on the results of the sequencing to determine what gets counted. In one aspect, an amount may be obtained based on a proportion of the sequenced output. For example, sequencing output corresponding to nucleic acid fragments of a specified size range could be selected after the bioinformatics analysis. Examples of the size ranges are about <300 bp, <200 by or <100 bp. Other examples include ranges of less than other values, such as 255 bp or other values between 300 by to 50 bp.

In step 150, a parameter is determined from the first amount and the second amount. The parameter may be, for example, a simple ratio of the first amount to the second amount, or the first amount to the second amount plus the first amount. In one aspect, each amount could be an argument to a function or separate functions, where a ratio may be then taken of these separate functions. One skilled in the art will appreciate the number of different suitable parameters.

In one embodiment, a parameter (e.g. a fractional representation of the clinically-relevant nucleic acids to the background nucleic acids) of a chromosome potentially involved in a chromosomal aneuploidy, e.g. chromosome 21 or chromosome 18 or chromosome 13, may then be calculated from the results of the bioinformatics procedure. The fractional representation may be obtained based on an amount of all of the sequences (e.g. some measure of all of the chromosomes including the clinically-relevant chromosome) or a particular subset of chromosomes (e.g. just one other chromosome than the one being tested.)

In step 150, the parameter is compared to one or more cutoff values. The cutoff values may be determined from any number of suitable ways. Such ways include Bayesian-type likelihood method, sequential probability ratio testing (SPRT), false discovery, confidence interval, receiver operating characteristic (ROC). Examples of applications of these methods and sample-specific methods are described in concurrently filed application "DETERMINING A NUCLEIC ACID SEQUENCE IMBALANCE,", Ser. No. 12/178,116, which is incorporated by reference.

In one embodiment, the parameter (e.g. the fractional representation of the clinically relevant chromosome) is then compared to a reference range established in pregnancies involving normal (i.e. euploid) fetuses. It is possible that in some variants of the procedure, the reference range (i.e. the cutoff values) would be adjusted in accordance with the fractional concentration of fetal DNA (f) in a particular maternal plasma sample. The value of f can be determined from the sequencing dataset, e.g. using sequences mappable to the Y chromosome if the fetus is male. The value off may also be determined in a separate analysis, e.g. using fetal epigenetic markers (Chan K C A et al 2006 Clin Chem 52, 2211-8) or from the analysis of single nucleotide polymorphisms.

In step 160, based on the comparison, a classification of whether a fetal chromosomal aneuploidy exists for the first chromosome is determined. In one embodiment, the classification is a definitive yes or no. In another embodiment, a classification may be unclassifiable or uncertain. In yet another embodiment, the classification may be a score that is to be interpreted at a later date, for example, by a doctor.

II. Sequencing, Aligning, and Determining Amounts

As mentioned above, only a fraction of the genome is sequenced. In one aspect, a pool of nucleic acids in a specimen is sequenced at <100% genomic coverage instead of at several folds of coverage, and among the proportion of captured nucleic acid molecules, most of each nucleic acid species is only sequenced once. Also, dosage imbalance of a particular chromosome or chromosomal regions can be quantitatively determined. In other words, the dosage imbalance of the chromosome or chromosomal regions is inferred from the percentage representation of the said locus among other mappable sequenced tags of the specimen.

This is contrasted from situations where the same pool of nucleic acids is sequenced multiple times to achieve high redundancy or several folds of coverage whereby each nucleic acid species is sequenced multiple times. In such situations, the number of times a particular nucleic acid species have been sequenced relative to that of another nucleic acid species correlate with their relative concentrations in the original sample. The sequencing cost increases with the number of fold coverage required to achieve accurate representation of the nucleic acid species.

In one example, a proportion of such sequences would be from the chromosome involved in an aneuploidy such as chromosome 21 in this illustrative example. Yet other sequences from such a sequencing exercise would be derived from the other chromosomes. By taking into account of the relative size of chromosome 21 compared with the other chromosomes, one could obtain a normalized frequency, within a reference range, of chromosome 21-specific sequences from such a sequencing exercise. If the fetus has trisomy 21, then the normalized frequency of chromosome 21-derived sequences from such a sequencing exercise will increase, thus allowing the detection of trisomy 21. The degree of change in the normalized frequency will be dependent on the fractional concentration of fetal nucleic acids in the analyzed sample.

In one embodiment, we used the Illumina Genome Analyzer for single-end sequencing of human genomic DNA and human plasma DNA samples. The Illumina Genome Analyzer sequences clonally-expanded single DNA molecules captured on a solid surface termed a flow cell. Each flow cell has 8 lanes for the sequencing of 8 individual specimens or pools of specimens. Each lane is capable of generating ~200 Mb of sequence which is only a fraction of the 3 billion basepairs of sequences in the human genome. Each genomic DNA or plasma DNA sample was sequenced using one lane of a flow cell. The short sequence tags generated were aligned to the human reference genome sequence and the chromosomal origin was noted. In one embodiment, perfect alignment is not required. The total number of individual sequenced tags aligned to each chromosome were tabulated and compared with the relative size of each chromosome as expected from the reference human genome or non-disease representative specimens. Chromosome gains or losses were then identified.

The described approach is only one exemplification of the presently described gene/chromosome dosage strategy. Alternatively, paired end sequencing could be performed. Instead of comparing the length of the sequenced fragments from that expected in the reference genome as described by Campbell et al (Nat Genet 2008; 40: 722-729), the number of aligned sequenced tags were counted and sorted according to chromosomal location. Gains or losses of chromosomal regions or whole chromosomes were determined by comparing the tag counts with the expected chromosome size in the reference genome or that of a non-disease representative specimen. As paired end sequencing allows one to deduce the size of the original nucleic acid fragment, one example is to focus on the counting of the number of paired sequenced tags corresponding to nucleic acid fragments of a specified size, such as <300 bp, <200 by or <100 bp.

In another embodiment, the fraction of the nucleic acid pool that is sequenced in a run is further sub-selected prior to sequencing. For example, hybridization based techniques such as oligonucleotide array could be used to first sub-select for nucleic acid sequences from certain chromosomes, e.g. a potentially aneuploid chromosome and other chromosome(s) not involved in the aneuploidy tested. Another example is that a certain sub-population of nucleic acid sequences from the sample pool is sub-selected or enriched prior to sequencing. For example, it has been reported that fetal DNA molecules in maternal plasma are comprised of shorter fragments than the maternal background DNA molecules (Chan et al Clin Chem 2004; 50: 88-92). Thus, one may use one or more methods known to those of skill in the art to fractionate the nucleic acid sequences in the sample according to molecule size, e.g. by gel electrophoresis or size exclusion columns or by microfluidics-based approach. Yet, alternatively, in the example of analyzing cell-free fetal DNA in maternal plasma, the fetal nucleic acid portion could be enriched by a method that suppresses the maternal background, such as by the addition of formaldehyde (Dhallan et al JAMA 2004; 291: 1114-9). In one embodiment, a portion or subset of the pre-selected pool of nucleic acids is sequenced randomly.

Other single molecule sequencing strategies such as that by the Roche 454 platform, the Applied Biosystems SOLiD platform, the Helicos True Single Molecule DNA sequencing technology, the single molecule, real-time (SMRT™) technology of Pacific Biosciences, and nanopore sequencing could similarly be used in this application.

III. Determining Amounts of Chromosomes from Sequencing Output

After the massively parallel sequencing, bioinformatics analysis was performed to locate the chromosomal origin of the sequenced tags. After this procedure, tags identified as originating from the potentially aneuploid chromosome, i.e. chromosome 21 in this study, are compared quantitatively to all of the sequenced tags or tags originating from one of more chromosomes not involved in the aneuploidy. The relationship between the sequencing output from chromosome 21 and other non-21 chromosomes for a test specimen is compared with cut-off values derived with methods described in the above section to determine if the specimen was obtained from a pregnancy involving a euploid or trisomy 21 fetus.

A number of different amounts include but not limited to the following could be derived from the sequenced tags. For example, the number of sequenced tags, i.e. absolute count, aligned to a particular chromosome could be compared to the absolute count of sequenced tags aligned to other chromosomes. Alternatively, the fractional count of the amount of sequenced tags from chromosome 21 with reference to all or some other sequenced tags could be compared to that of other non-aneuploid chromosomes. In the present experiment, because 36 by were sequenced from each DNA fragment, the number of nucleotides sequenced from a particular chromosome could easily be derived from 36 by multiplied by the sequenced tag count.

Furthermore, as each maternal plasma specimen was only sequenced using one flow cell which could only sequence a fraction of the human genome, by statistics, most of the maternal plasma DNA fragment species would only each have been sequenced to generate one sequenced tag count. In other words, the nucleic acid fragments present in the maternal plasma specimen were sequenced at less than 1-fold coverage. Thus, the total number of sequenced nucleotides for any particular chromosome would mostly correspond to the amount, proportion or length of the part of the said chromosome that has been sequenced. Hence, the quantitative determination of the representation of the potentially aneuploid chromosome could be derived from a fraction of the number or equivalent length of nucleotides sequenced from that chromosome with reference to a similarly derived quantity for other chromosomes.

Counting Based on Length

As described in examples II and IV below, a subset of the sequenced data is sufficient to distinguish trisomy 21 from euploid cases. The subset of sequenced data could be the proportion of sequenced tags that passed certain quality parameters. For example, in example II, sequenced tags that were uniquely aligned to the repeat-masked reference human genome were used. Alternatively, one may sequence a representative pool of nucleic acid fragments from all of the chromosomes but focus on the comparison between data relevant to the potentially aneuploid chromosome and data relevant to a number of non-aneuploid chromosomes. Yet alternatively, a subset of the sequencing output encompassing sequenced tags generated from nucleic acid fragments corresponding to a specified size window in the original specimen could be sub-selected during the post-sequencing analysis.

Figure 1B:
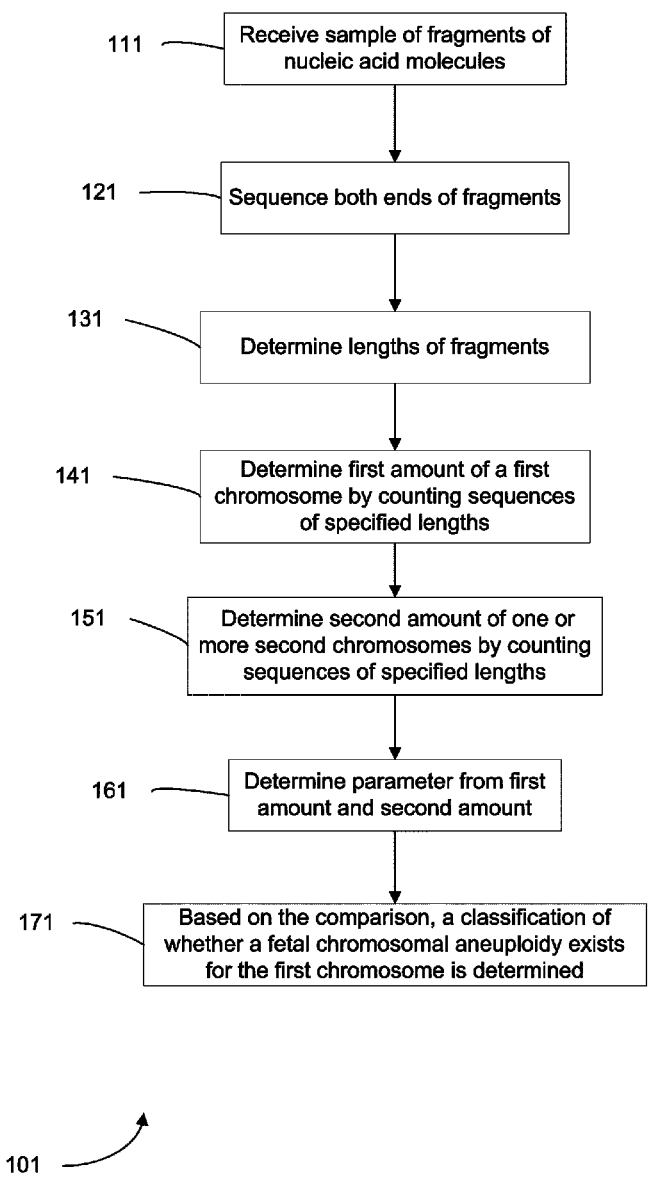
FIG. 1B is a flowchart of a method 101 for performing prenatal diagnosis of a fetal chromosomal aneuploidy in a biological sample obtained from a pregnant female subject according to an embodiment of the present invention.

FIG. 1B is a flowchart of another method 101 for performing prenatal diagnosis of a fetal chromosomal aneuploidy in a biological sample obtained from a pregnant female subject according to an embodiment of the present invention.

In step 111, a biological sample from the pregnant female is received. The sample contains nucleic acid molecules from the fetus and the pregnant female. For example, the nucleic acid molecules may be fragments from chromosomes.

In step 121, at least a portion of a plurality of the nucleic acid molecules contained in the biological sample are sequenced. In one embodiment, the nucleic acid molecules are fragments of respective chromosomes. At least both ends of the fragments are sequenced, and the entire fragment may be sequenced. All of the nucleic acid molecules in the sample may be sequenced, or just a subset may be sequenced. This subset may be randomly chosen, as will be described in more detail later. In one embodiment, the Illumina Genome analyzer is used to perform the paired-end sequencing to sequence the two ends of nucleic acid fragments.

In step 131, the length of each fragment is determined. In one embodiment, the sequenced data from each paired-end are aligned to a reference sequence (e.g. the reference human genome sequence), e.g., using BLAST. The distance or number of nucleotides spanning between the two ends is then determined to be the length of the sequenced fragment. Effectively, the whole fragment is sequenced by performing the alignment. Thus, the length of the sequences of the fragment is deduced.

Alternatively, sequencing platforms such as the 454 platform and possibly some single molecule sequencing techniques are able to sequence the full length of short nucleic acid fragments, for example 200 by or equivalently nucleotides (nt). In this manner, the actual length of the nucleic acid fragment would be immediately known from the sequenced data.

Such paired-end analysis is also possible using other sequencing platforms, e.g. the Applied Biosystems SOLiD system. For the Roche 454 platform, because of its increased read length compared with other massively parallel sequencing systems, it is also possible to determine the length of a fragment from its complete sequence.

In step 141, based on the sequencing and the lengths, a first amount of a first chromosome is determined. In one embodiment, fragments of a specified length are counted. The specified length may be a specific number of nucleotides (or base pairs) or a range of lengths. For example, the length may be specified to be greater than or less than a number, or greater (less) than or equal to the number. As another example, the range may specified to be between two numbers, and optionally including the numbers.

The counted fragments are associated with a particular chromosome, for example, as may be done during the alignment procedure. The first amount is thus determined from sequences that are identified as originating from the first chromosome and that are of the specified length. In one aspect, a proportion of such counted sequences may be discarded from the amount because they are present in the repeat regions of the human genome, or in regions subjected to inter-individual variations, e.g. copy number variations.

In step 151, based on the sequencing and the lengths, a second amount of one or more second chromosomes is determined from sequences identified as originating from one of the second chromosomes. In one embodiment, the specified length for the fragments counted to determine the second amount is a different specified length than the specified length used to determine the first amount, as in step 141. Different lengths may be used for different chromosomes as well. All of the ways of determining the amounts from method 100 may also be used for method 100.

In step 151, a parameter is determined from the first amount and the second amount. The parameter may be as described for method 100 and other places herein. In step 161, the parameter is compared to one or more cutoff values. The cutoff values may be determined from any number of suitable ways, as in method 100 and other places herein.

In step 171, based on the comparison, a classification of whether a fetal chromosomal aneuploidy exists for the first chromosome is determined. In one embodiment, the classification is a definitive yes or no. In another embodiment, a classification may be unclassifiable or uncertain. In yet another embodiment, the classification may be a score that is to be interpreted at a later date, for example, by a doctor.

In further embodiments, certain chromosomes may be selected to be used as the second chromosomes for determining the second amount and the parameter that is compared to the cutoff values. For example, the second chromosomes may be selected to have similar properties as the first chromosome. In one embodiment, the second chromosomes are selected such that the nucleic acid molecules (i.e. fragments) of the one or more second chromosomes have an expected average length that is within two nucleotides of the expected average length for the first chromosome. In another embodiment, the nucleic acid molecules of the one or more second chromosomes have an expected maximum and minimum length that are both within two nucleotides of the expected maximum and minimum length for the first chromosome.

In other embodiments, the second chromosomes have different properties which may be accounted for. For example, the second chromosomes may have different lengths of fragments than the first chromosome. The second chromosomes may also have different properties amongst themselves. In one embodiment, the different properties is accounted for by selecting sequences that originate from at least one of the second chromosomes to be of a different specified length (e.g. less than a different number of nt) than the sequences of the first chromosome. In one aspect, the different specified length is selected based on an expected size distribution for the nucleic acid molecules of the least one of the second chromosomes that are in the biological sample.

In one embodiment, the specified length for counting focuses on short nucleic acid fragments. An advantage of focusing the data analysis on the subset of sequenced tags corresponding to short nucleic acid fragments in the original maternal plasma specimen is because the dataset would effectively be enriched with DNA sequences derived from the fetus. This is because the fetal DNA molecules in maternal plasma are comprised of shorter fragments than the maternal background DNA molecules (Chan et al Clin Chem 2004; 50: 88-92).

According to FIG. 7, the number of sequenced tags required for differentiating euploid from trisomy 21 cases would reduce as the fractional fetal DNA concentration increases. However, the increase of the fractional fetal DNA concentration by counting only smaller fragments comes at a cost of providing a fewer number of total sequences, which can cause statistical fluctuations and errors in the classification, e.g., false positives. Accordingly, in one embodiment, the one or more specified lengths (potentially for different chromosomes per above) for counting the fragments are selected to provide at least a specific total amount for the first amount and the second amount. In different embodiments, the total amount is two million, 1 million, 500,000, or 250,000.

Also, the one or more specified lengths for counting the fragments may be selected to balance an increase in the percentage of sequenced fetal fragments and the total number of sequences. In an embodiment where sequences from the first chromosome are counted if they are less than a first predetermined number of nucleotides, the first specified number of nucleotides selected to be between about 125 nucleotides and about 175 nucleotides. Such a selection can provide such a balance.

In another embodiment, the sequences that originate from the first chromosome are selected to be greater than a second specified number of nucleotides. In one aspect, the second specified number is between 100 and 125 nucleotides. In another aspect, such a minimum length can provide for greater accuracy. For example, a benefit is to remove the ultra-short fragments that are generated in vitro, e.g., by DNA degradation, instead of genuinely present in plasma in the in vivo state. The sequences that originate from at least one of the second chromosomes may also selected to be greater than a specified number of nucleotides, which may be different than the second specified number. Example II below provides data regarding optimal lengths to be used for counting the fragments.

As another advantage, the post-sequencing selection of subsets of nucleic acid pools is different from other nucleic acid enrichment strategies which are performed prior to specimen analysis, such as the use gel electrophoresis or size exclusion columns for the selection of nucleic acids of particular sizes, which require the physical separation of the enriched pool from the background pool of nucleic acids. The physical procedures would introduce more experimental steps and may be prone to problems such as contamination. The post-sequencing in silico selection of subsets of sequencing output would also allow one to vary the selection depending on the sensitivity and specificity required for disease determination.

IV. Enrichment for Pools of Nucleic Acids for Sequencing

As mentioned above and established in the example section below, only a portion of the human genome needs to be sequenced to differentiate trisomy 21 from euploid cases. Thus, it would be possible and cost-effective to enrich the pool of nucleic acids to be sequenced prior to random sequencing of a fraction of the enriched pool. For example, fetal DNA molecules in maternal plasma are comprised of shorter fragments than the maternal background DNA molecules (Chan et al Clin Chem 2004; 50: 88-92). Thus, one may use one or more methods known to those of skill in the art to fractionate the nucleic acid sequences in the sample according to molecule size (e.g. by number of nucleotides), e.g. by gel electrophoresis (Li et al Clin Chem 2004; 50: 1002-1011) or size exclusion columns or by microfluidics-based approach. The specific sizes (e.g. lengths) chosen for the fractionating may be the same specified lengths used for the counting described above.

Yet, alternatively, in the example of analyzing cell-free fetal DNA in maternal plasma, the fetal nucleic acid portion could be enriched by a method that suppresses the maternal background, such as by the addition of formaldehyde (Dhallan et al JAMA 2004; 291: 1114-9). The proportion of fetal derived sequences would be enriched in the nucleic acid pool comprised of shorter fragments. According to FIG. 7, the number of sequenced tags required for differentiating euploid from trisomy 21 cases would reduce as the fractional fetal DNA concentration increases.

Alternatively, sequences originating from a potentially aneuploid chromosome and one or more chromosomes not involved in the aneuploidy could be enriched by hybridization techniques for example onto oligonucleotide microarrays. Examples of commercially available products for allowing such enrichment by hybridization includes the NimbleGen Sequence Capture microarrays and Agilent SureSelect Target Enrichment System. The enriched pools of nucleic acids would then be subjected to random sequencing. This would allow the reduction in sequencing costs.

V. Random Sequencing

Figure 2:
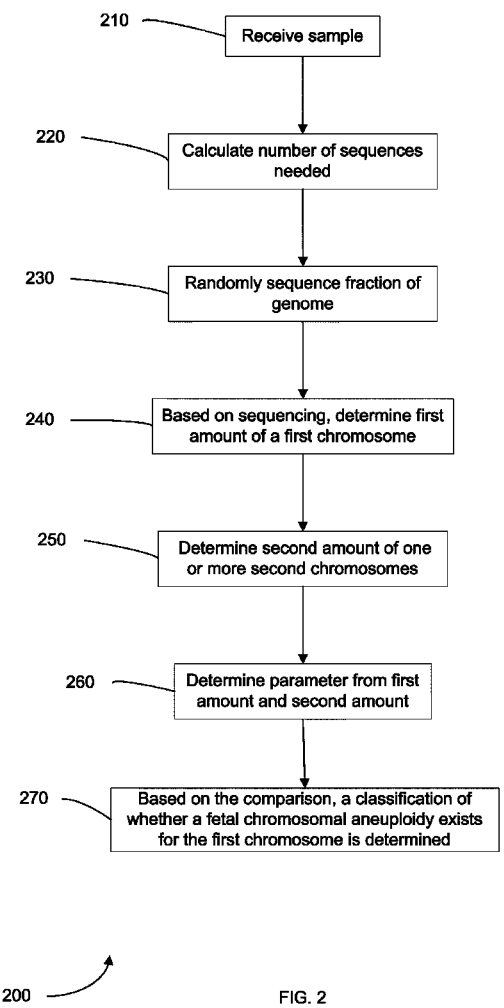
FIG. 2 is a flowchart of a method 200 for performing prenatal diagnosis of a fetal chromosomal aneuploidy using random sequencing according to an embodiment of the present invention.

FIG. 2 is a flowchart of a method 200 for performing prenatal diagnosis of a fetal chromosomal aneuploidy using random sequencing according to an embodiment of the present invention. In one aspect for the massively parallel sequencing approach, representative data from all of the chromosomes may be generated at the same time. The origin of a particular fragment is not selected ahead of time. The sequencing is done at random and then a database search may be performed to see where a particular fragment is coming from. This is contrasted from situations when a specific fragment from chromosome 21 and another one from chromosome 1 are amplified.

In step 210, a biological sample from the pregnant female is received. In step 220, the number N of sequences to be analyzed is calculated for a desired accuracy. In one embodiment, a percentage of fetal DNA in the biological sample is first identified. This may be done by any suitable means as will be known to one skilled in the art. The identification may simply be reading a value that was measured by another entity. In this embodiment, the calculation of the number N of sequences to be analyzed is based on the percentage. For example, the number of sequences needed to be analyzed would be increased when the fetal DNA percentage drops, and could be decreased when the fetal DNA rises. The number N may be a fixed number or a relative number, such as a percentage. In another embodiment, one could sequence a number N that is known to be adequate for accurate disease diagnosis. The number N could be made sufficient even in pregnancies with fetal DNA concentrations that are at the lower end of the normal range.

In step 230, at least N of a plurality of the nucleic acid molecules contained in the biological sample are randomly sequenced. A feature of this described approach is that the nucleic acids to be sequenced are not specifically identified or targeted before sample analysis, i.e. sequencing. Sequence-specific primers to target specific gene loci are not needed for sequencing. The pools of nucleic acids sequenced vary from sample to sample and even from analysis to analysis for the same sample. Furthermore, from the below descriptions, the amount of sequencing output required for case diagnosis could vary between the tested specimens and the reference population. These aspects are in marked contrast to most molecular diagnostic approaches, such as those based on fluorescence in situ hybridization, quantitative florescence PCR, quantitative real-time PCR, digital PCR, comparative genomic hybridization, microarray comparative genomic hybridization and so on, where gene loci to be targeted require prior pre-determination, thus requiring the use of locus-specific primers or probe sets or panels of such.

In one embodiment, random sequencing is performed on DNA fragments that are present in the plasma of a pregnant woman, and one obtains genomic sequences which would originally have come from either the fetus or the mother. Random sequencing involves sampling (sequencing) a random portion of the nucleic acid molecules present in the biological sample. As the sequencing is random, a different subset (fraction) of the nucleic acid molecules (and thus the genome) may be sequenced in each analysis. Embodiments will work even when this subset varies from sample to sample and from analysis to analysis, which may occur even using the same sample. Examples of the fraction are about 0.1%, 0.5%, 1%, 5%, 10%, 20%, or 30% of the genome. In other embodiments, the fraction is at least any one of these values.

The rest of the steps 240-270 may proceed in a similar manner as method 100.

Figure 10:
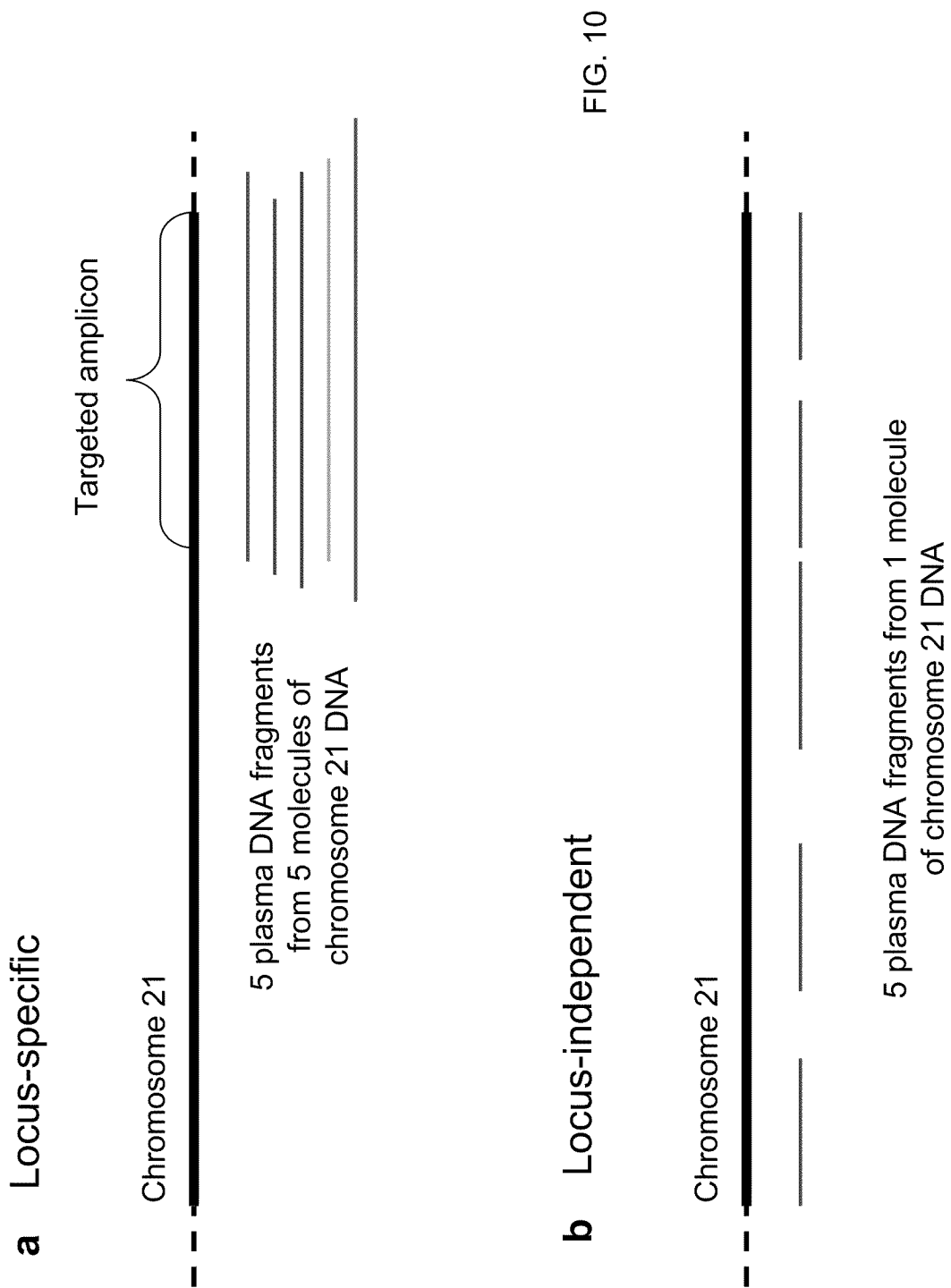
FIGS. 10a and 10b shows a schematic comparison between locus-specific and locus-independent methods for DNA quantification.

Regarding the use (or non-use) of a locus to identify an identity of a fragment, FIG. 10 shows a schematic comparison between locus-specific and locus-independent methods (e.g. methods described herein) for DNA quantification.

DNA molecules exist as short fragments in maternal plasma. Hence, instead of comparing the relative amounts between specific loci as with conventional DNA quantification methods, the amount of quantitative information that one could derive with the same amount of plasma DNA input greatly increases with the use of locus-independent quantification methods that treat each DNA fragment as an individual target. For example, as depicted in FIG. 10a, when using locus-specific assays, five copies of chromosome 21 with the targeted amplicon region intact would be needed to be physically present to generate a count of five. However, as shown in FIG. 10b, in the locus-independent method, five fragmented portions originating from a single chromosome 21 could potentially contribute to a count of five.

The bioinformatics, computational and statistical approaches used to determine if a maternal plasma specimen is obtained from a pregnant woman conceived with a trisomy 21 or euploid fetus could be compiled into a computer program product used to determine parameters from the sequencing output. The operation of the computer program would involve the determining of a quantitative amount from the potentially aneuploid chromosome as well as amount(s) from one or more of the other chromosomes. A parameter would be determined and compared with appropriate cut-off values to determine if a fetal chromosomal aneuploidy exists for the potentially aneuploid chromosome.

EXAMPLES

The following examples are offered to illustrate, but not to limit the claimed invention.

I. Prenatal Diagnosis of Fetal Trisomy 21

Eight pregnant women were recruited for the study. All of the pregnant women were in the $1^{st}$ or $2^{nd}$ trimester of gestation and had a singleton pregnancy. Four of them were each carrying a fetus with trisomy 21 and the other four were each carrying a euploid fetus. Twenty milliliters of peripheral venous blood were collected from each subject. Maternal plasma was harvested after centrifugation at 1600×g for 10 minutes and further centrifuged at 16000×g for 10 minutes. DNA was then extracted from 5-10 mL of each plasma sample. The maternal plasma DNA was then used for massively parallel sequencing by the Illumina Genome Analyzer according to manufacturer's instructions. The technicians performing the sequencing were blinded from the fetal diagnoses during the sequencing and sequence data analysis.

Briefly, approximately 50 ng of maternal plasma DNA was used for DNA library preparation. It is possible to start with lesser amounts such as 15 ng or 10 ng of maternal plasma DNA. Maternal plasma DNA fragments were blunt-ended, ligated to Solexa adaptors and fragments of 150-300 by were selected by gel purification. Alternatively, blunt-ended and adaptor-ligated maternal plasma DNA fragments could be passed through columns (e.g. AMPure, Agencourt) to remove unligated adaptors without size-selection before cluster generation. The adaptor-ligated DNA was hybridized to the surface of flow cells, and DNA clusters were generated using the Illumina cluster station, followed by 36 cycles of sequencing on the Illumina Genome Analyzer. DNA from each maternal plasma specimen was sequenced by one flow cell. Sequenced reads were compiled using Solexa Analysis Pipeline. All reads were then aligned to the repeat-masked reference human genomic sequence, NCBI 36 assembly (GenBank accession numbers: NC_000001 to NC_000024), using the Eland application.

In this study, to reduce the complexity of the data analysis, only sequences that have been mapped to a unique location in the repeat-masked human genome reference are further considered. Other subsets of or the entire set of the sequenced data could alternatively be used. The total number of uniquely mappable sequences for each specimen was counted. The number of sequences uniquely aligned to chromosome 21 was expressed as a proportion to the total count of aligned sequences for each specimen. As maternal plasma contains fetal DNA among a background of DNA of maternal origin, the trisomy 21 fetus would contribute extra sequenced tags originating from chromosome 21 due to the presence of an extra copy of chromosome 21 in the fetal genome. Hence, the percentage of chromosome 21 sequences in maternal plasma from a pregnancy carrying a trisomy 21 fetus would be higher than that from a pregnancy with a euploid fetus. The analysis does not require the targeting of fetal-specific sequences. It also does not require the prior physical separation of fetal from maternal nucleic acids. It also does not require the need to distinguish or identify fetal from maternal sequences after sequencing.

Figure 3A:
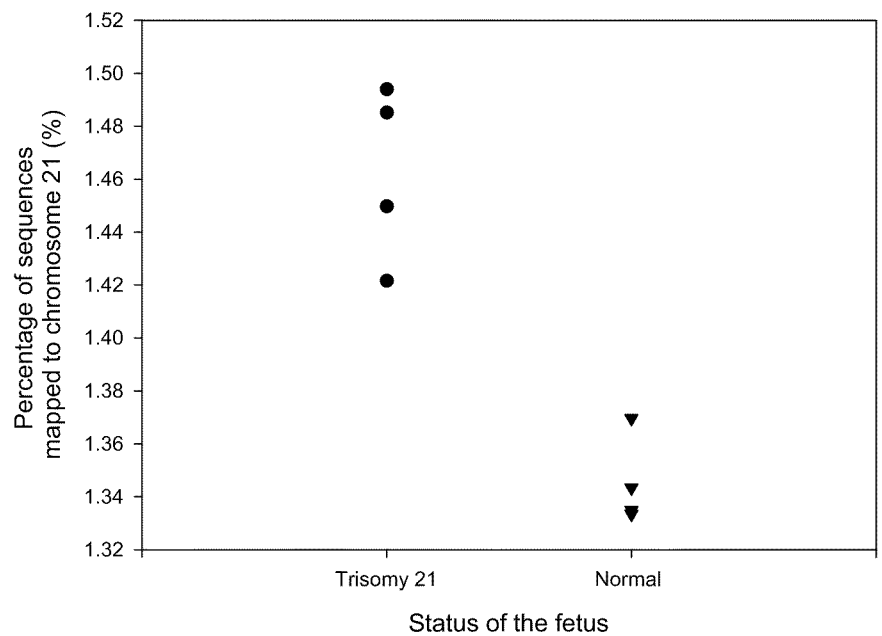
FIG. 3A shows a plot of percentage representation of chromosome 21 sequences in maternal plasma samples involving trisomy 21 or euploid fetuses according to an embodiment of the present invention.

FIG. 3A shows the percentage of sequences mapped to chromosome 21 (percentage representation of chromosome 21) for each of the 8 maternal plasma DNA samples. The percentage representation of chromosome 21 was significantly higher in maternal plasma of trisomy 21 pregnancies than in that of euploid pregnancies. These data suggest that noninvasive prenatal diagnosis of fetal aneuploidy could be achieved by determining the percentage representation of the aneuploid chromosome compared to that of a reference population. Alternatively, the chromosome 21 over-representation could be detected by comparing the percentage representation of chromosome 21 obtained experimentally with the percentage representation of chromosome 21 sequences expected for a euploid human genome. This could be done by masking or not masking the repeat regions in the human genome.

Five of the eight pregnant women were each carrying a male fetus. The sequences mapped to the Y chromosome would be fetal-specific. The percentage of sequences mapped to the Y-chromosome was used to calculate the fractional fetal DNA concentration in the original maternal plasma specimen. Moreover, the fractional fetal DNA concentration was also determined by using microfluidics digital PCR involving the zinc finger protein, X-linked (ZFX) and zinc finger protein, Y-linked (ZFY) paralogous genes.

Figure 3B:
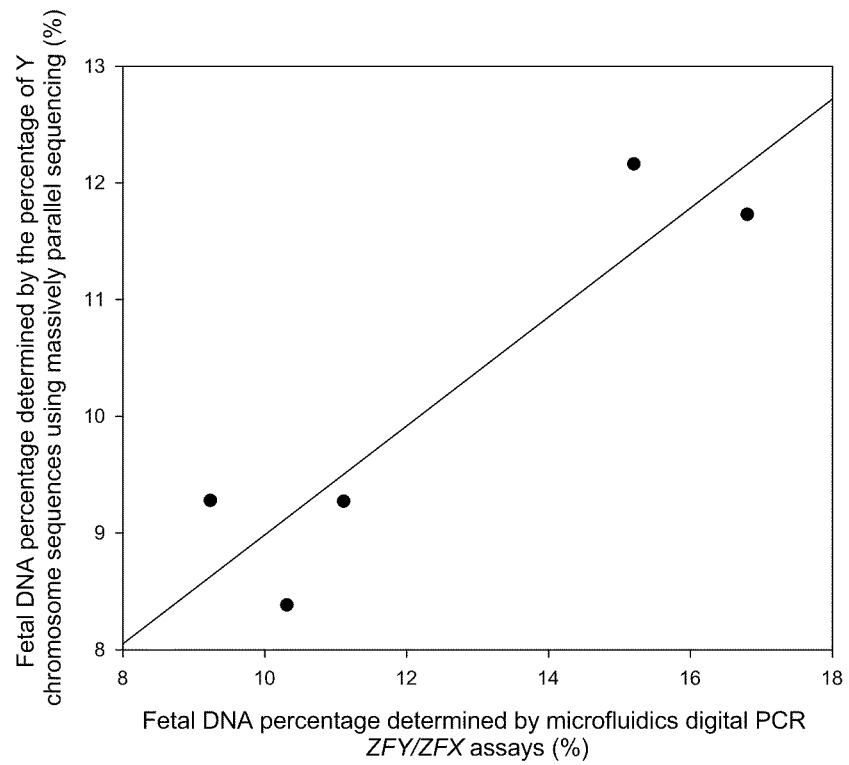
FIG. 3B shows a correlation between maternal plasma fractional fetal DNA concentrations determined by massively parallel sequencing and microfluidics digital PCR according to an embodiment of the present invention.

FIG. 3B shows the correlation of the fractional fetal DNA concentrations as inferred by the percentage representation of Y chromosome by sequencing and that determined by ZFY/ZFX microfluidics digital PCR. There was a positive correlation between the fractional fetal DNA concentrations in maternal plasma determined by these two methods. The coefficient of correlation (r) was 0.917 in the Pearson correlation analysis.

Figure 4A:
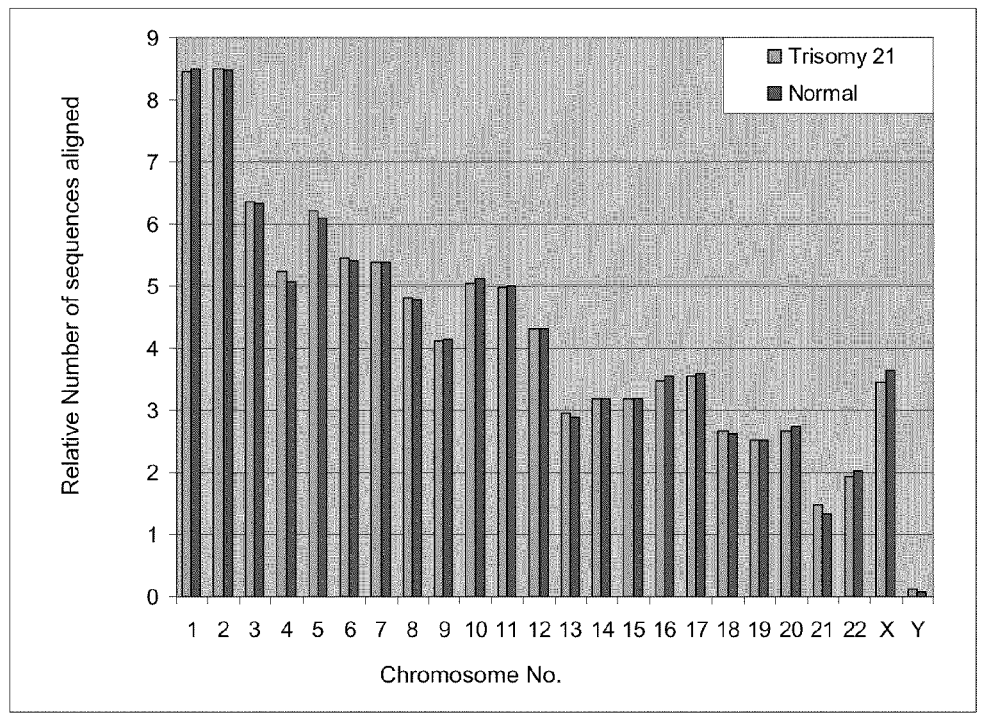
FIG. 4A shows a plot of percentage representation of aligned sequences per chromosome according to an embodiment of the present invention.

The percentages of maternal plasma DNA sequences aligned to each of the 24 chromosomes (22 autosomes and X and Y chromosomes) for two representative cases are shown in FIG. 4A. One pregnant woman was carrying a trisomy 21 fetus and the other was carrying a euploid fetus. The percentage representation of sequences mapped to chromosome 21 is higher in the pregnant woman carrying a trisomy 21 fetus when compared with the pregnant woman carrying a normal fetus.

Figure 4B:
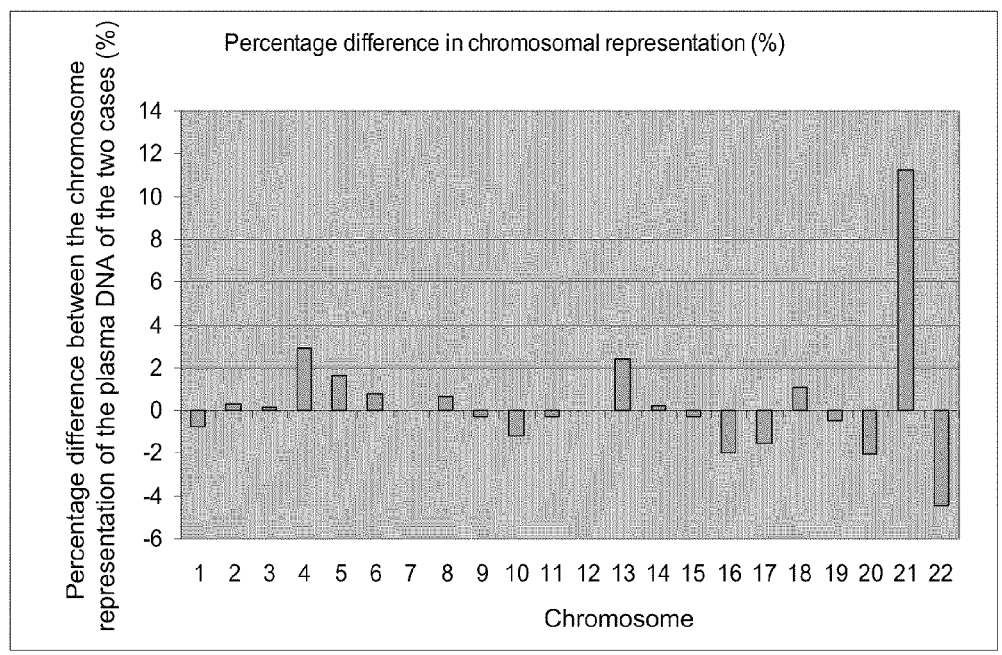
FIG. 4B shows a plot of difference (%) in percentage representation per chromosome between the trisomy 21 case and euploid case shown in FIG. 4A.

The differences (%) of the percentage representation per chromosome between the maternal plasma DNA specimens of the above two cases is shown in FIG. 4B. The percentage difference for a particular chromosome is calculated using the formula below:

Percentage difference (%)=$(P_{21}-P_E)/P_E \times 100\%$, where $P_{21}$=percentage of plasma DNA sequences aligned to the particular chromosome in the pregnant woman carrying a trisomy 21 fetus and;
$P_E$=percentage of plasma DNA sequences aligned to the particular chromosome in the pregnant woman carrying a euploid fetus.

As shown in FIG. 4B, there is an over-representation of chromosome 21 sequences by 11% in the plasma of the pregnant woman carrying a trisomy 21 fetus when compared with the pregnant woman carrying a euploid fetus. For the sequences aligned to other chromosomes, the differences between the two cases were within 5%. As the percentage representation for chromosome 21 is increased in the trisomy 21 compared with the euploid maternal plasma samples, the difference (%) could be alternatively referred as the degree of over-representation in chromosome 21 sequences. In addition to differences (%) and absolute differences between the chromosome 21 percentage representation, ratios of the counts from test and reference samples could also be calculated and would be indicative of the degree of chromosome 21 over-representation in trisomy 21 compared with euploid samples.

For the four pregnant women each carrying a euploid fetus, a mean of 1.345% of their plasma DNA sequences were aligned to chromosome 21. In the four pregnant women carrying a trisomy 21 fetus, three of their fetuses were males. The percentage representation of chromosome 21 was calculated for each of these three cases. The difference (%) in chromosome 21 percentage representation for each of these three trisomy 21 cases from the mean chromosome 21 percentage representation derived from values of the four euploid cases were determined as described above. In other words, the mean of the four cases carrying a euploid fetus was used as the reference in this calculation. The fractional fetal DNA concentrations for these three male trisomy 21 cases were inferred from their respective percentage representation of Y chromosome sequences.

Figure 5:
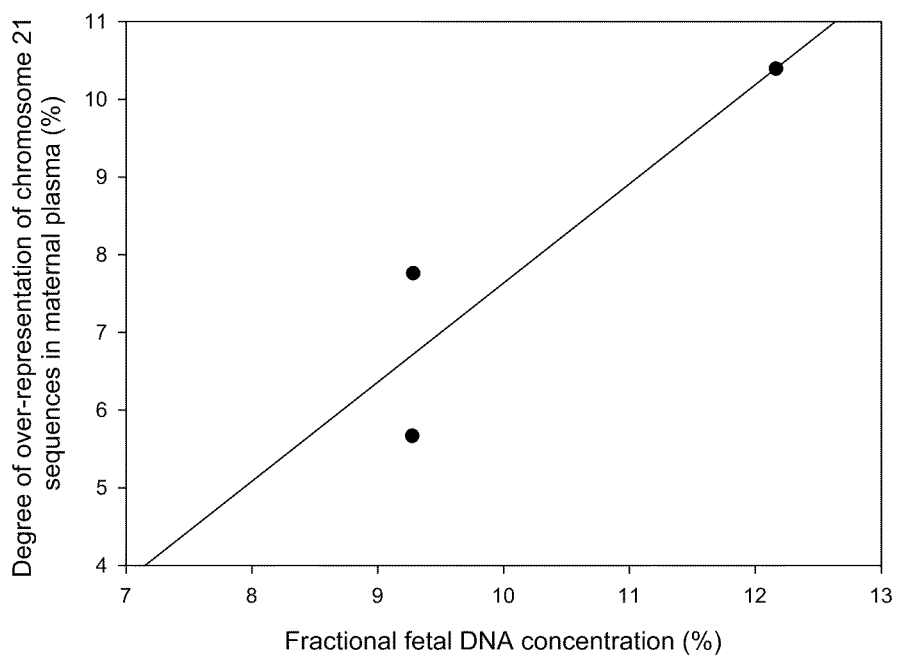
FIG. 5 shows a correlation between degree of over-representation in chromosome 21 sequences and the fractional fetal DNA concentrations in maternal plasma involving trisomy 21 fetuses according to an embodiment of the present invention.

The correlation between the degree of over-representation for chromosome 21 sequences and the fractional fetal DNA concentrations is shown in FIG. 5. There was a significant positive correlation between the two parameters. The coefficient of correlation (r) was 0.898 in the Pearson correlation analysis. These results indicate that the degree of over-representation of chromosome 21 sequences in maternal plasma is related to the fractional concentration of fetal DNA in the maternal plasma sample. Thus, cut-off values in the degree of chromosome 21 sequence over-representation relevant to the fractional fetal DNA concentrations could be determined to identify pregnancies involving trisomy 21 fetuses.

The determination of the fractional concentration of fetal DNA in maternal plasma can also be done separate to the sequencing run. For example, the Y chromosome DNA concentration could be pre-determined using real-time PCR, microfluidics PCR or mass spectrometry. For example, we have demonstrated in FIG. 3B that there is good correlation between the fetal DNA concentrations estimated based on the Y-chromosome count generated during the sequencing run and the ZFY/ZFX ratio generated external to the sequencing run. In fact, fetal DNA concentration could be determined using loci other than the Y chromosome and applicable to female fetuses. For example, Chan et al showed that fetal-derived methylated RASSF1A sequences would be detected in the plasma of pregnant women in the background of maternally derived unmethylated RASSF1A sequences (Chan et al, Clin Chem 2006; 52:2211-8). The fractional fetal DNA concentration can thus be determined by dividing the amount of methylated RASSF1A sequences by the amount of total RASSF1A (methylated and unmethylated) sequences.

It is expected that maternal plasma would be preferred over maternal serum for practicing our invention because DNA is released from the maternal blood cells during blood clotting. Thus, if serum is used, it is expected that the fractional concentration of fetal DNA will be lower in maternal plasma than maternal serum. In other words, if maternal serum is used, it is expected that more sequences would need to be generated for fetal chromosomal aneuploidy to be diagnosed, when compared with a plasma sample obtained from the same pregnant woman at the same time.

Yet another alternative way of determining the fractional concentration of fetal DNA would be through the quantification of polymorphic differences between the pregnant women and the fetus (Dhallan R, et al. 2007 *Lancet*, 369, 474-481). An example of this method would be to target polymorphic sites at which the pregnant woman is homozygous and the fetus is heterozygous. The amount of fetal-specific allele can be compared with the amount of the common allele to determine the fractional concentration of fetal DNA.

In contrast to the existing techniques for detecting chromosomal aberrations, including comparative genomic hybridization, microarray comparative genomic hybridization, quantitative real-time polymerase chain reaction, which detect and quantify one or more specific sequence(s), massively parallel sequencing is not dependent on the detection or analysis of predetermined or a predefined set of DNA sequences. A random representative fraction of DNA molecules from the specimen pool is sequenced. The number of different sequenced tags aligned to various chromosomal regions is compared between specimens containing or not containing the DNA species of interest. Chromosomal aberrations would be revealed by differences in the number (or percentage) of sequences aligned to any given chromosomal region in the specimens.

In another example the sequencing technique on plasma cell-free DNA may be used to detect the chromosomal aberrations in the plasma DNA for the detection of a specific cancer. Different cancers have a set of typical chromosomal aberrations. Changes (amplifications and deletions) in multiple chromosomal regions may be used. Thus, there would be an increased proportion of sequences aligned to the amplified regions and a decreased proportion of sequences aligned to decreased regions. The percentage representation per chromosome could be compared with the size for each corresponding chromosome in a reference genome expressed as percentage of genomic representation of any given chromosome in relation to the whole genome. Direct comparisons or comparisons to a reference chromosome may also be used.

In another example, DNA from 5 mL to 10 mL plasma from 14 trisomy 21 and 14 euploid pregnancies was used. A random representative portion of DNA molecules in the maternal plasma is sequenced. A mean of ~2 million unique reads per sample was obtained, without mismatches (mismatches of 1 or 2 may also be allowed) to the reference human genome. The chromosomal origin of each sequenced read is identified by bioinformatics analysis.

The mean and standard deviation of the proportion of reads from each chromosome of a reference sample set comprising pregnancies with euploid male fetuses are determined. Z-scores, representing the number of standard deviations from the mean of the reference sample set, of the percentage chromosomal representation for each maternal plasma sample was calculated. The number of reads originating from chromosome 21 was expressed as a proportion of all sequenced reads, and z-scores, representing the number of standard deviations away from the mean proportion of chromosome 21 reads in a reference set of euploid cases, were determined for each case.

Figure 11:
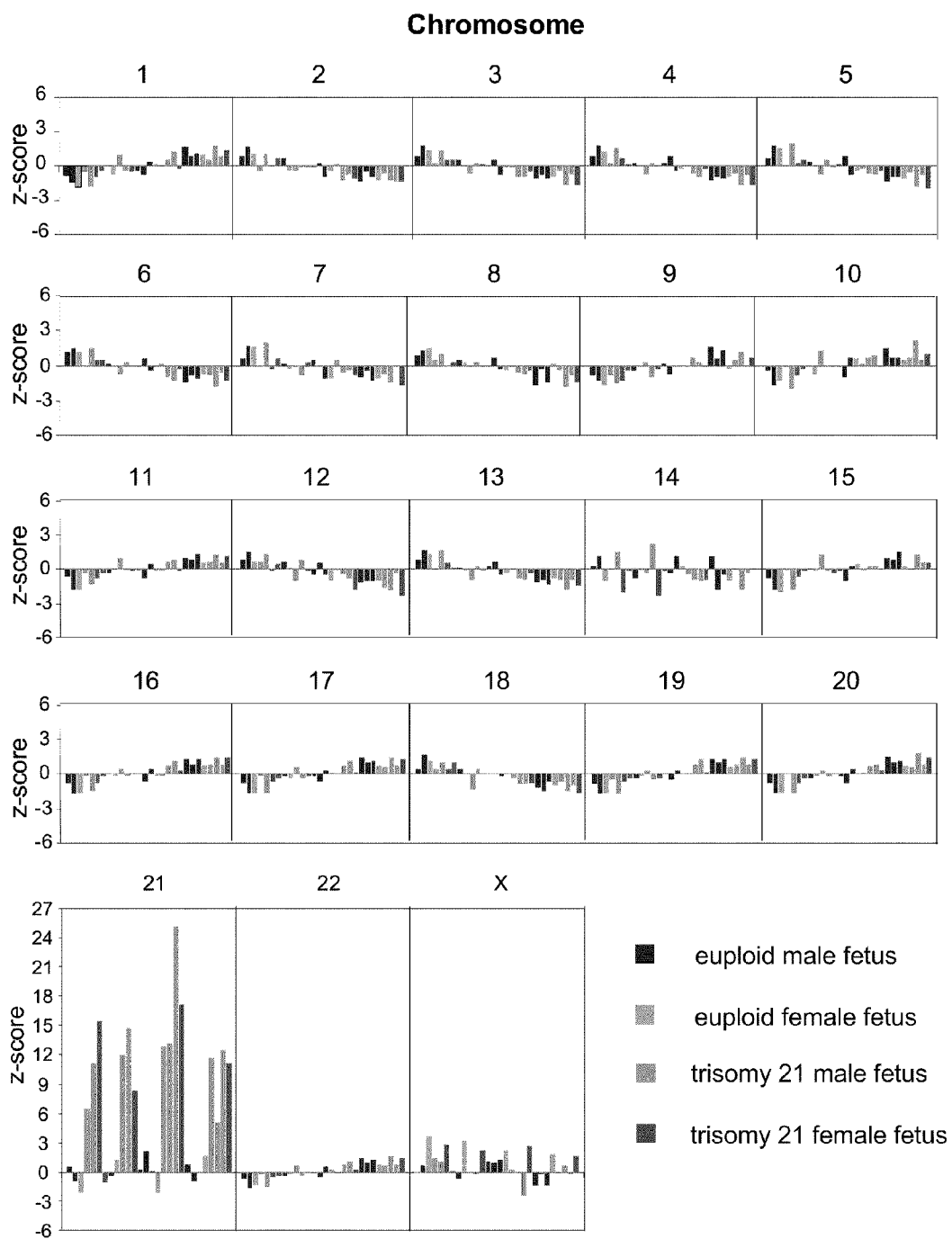
FIG. 11 shows plots of z-scores for each chromosome for maternal plasma samples from 14 trisomy 21 and 14 euploid pregnancies according to an embodiment of the present invention.

FIG. 11 shows plots of z-scores for each chromosome for maternal plasma samples from 14 trisomy 21 and 14 euploid pregnancies are shown. The different types (i.e. euploid or trisomy) of samples are categorized. Each of the 28 bars shown for each chromosome corresponded to the z-scores for one of the 28 maternal plasma samples. Samples 1 to 28 are shown consecutively from left to right.

A z-score larger than ±3 indicated a 99% chance of a statistically significant difference in the assessed parameter for the test case compared with the reference group (e.g. presence of chromosomal over- or underrepresentation compared with the reference group). Thus, a high z-score was expected for trisomy 21 cases. The massively parallel sequencing approach was reliable and robust: in all cases, z-scores smaller than ±3 were obtained for all chromosomes except 21 and X (FIG. 11). Z-scores of chromosome 21 were beyond +5 for all 14 trisomy 21 cases but within ±3 for all euploid cases. Because pregnancies with male fetuses were used as the reference sample set, z-scores for the X-chromosome were increased in all pregnancies with female fetuses.

II. Sequencing Just a Fraction of the Human Genome

In the experiment described in example I above, maternal plasma DNA from each individual specimen was sequenced using one flow cell only. The number of sequenced tags generated from each of the tested specimens by the sequencing run is shown in FIG. 6. T21 denotes a sample obtained from a pregnancy involving a trisomy 21 fetus.

As 36 by were sequenced from each of the sequenced maternal plasma DNA fragments, the number of nucleotides/basepairs sequenced from each specimen could be determined by 36 by multiplied by the sequenced tag count and are also shown in FIG. 6. As there are approximately 3 billion basepairs in the human genome, the amount of sequencing data generated from each maternal plasma specimen represented only a fraction, ranging from some 10% to 13%.

Furthermore, in this study, only the uniquely mappable sequenced tags, termed U0 in nomenclature from the Efficient Large-Scale Alignment of Nucleotide Databases (ELAND) software, were used to demonstrate the presence of over-representation in the amount of chromosome 21 sequences in the maternal plasma specimens from pregnancies each carrying a fetus with trisomy 21, as described in example I above. As shown in FIG. 6, U0 sequences only represent a subset of all the sequenced tags generated from each specimen and further represent an even smaller proportion, some 2%, of the human genome. These data indicate that the sequencing of only a portion of the human genomic sequences present in the tested specimen is sufficient to achieve the diagnosis of fetal aneuploidy.

III. Paired-End Sequencing and Length Dependent Counting

In this example, paired-end (PE) sequencing was applied directly, without fragmentation and gel electrophoresis based size selection, for sequencing of plasma from pregnancies with euploid or trisomy 21 fetuses. As described above, the nucleotide length, i.e. size, of each fragment was deduced from the alignment positions of the sequenced ends of each plasma DNA molecule.

Detection of Chromosome Dosage with Paired-End Sequencing

The ability to detect fetal DNA by paired-end sequencing is first established. Placental tissue DNA from two euploid fetuses and two T21 fetuses were sequenced. The proportion of accepted PE reads for each chromosome was close to that expected for the human genome (data not shown). 1.82% and 1.85% of PE reads from chr21 were obtained from the two T21 placental tissue samples, respectively, which were ±1.5-fold higher than the proportions for the two euploid samples (1.28% and 1.30%, respectively). These data suggested that the measurement of chromosome dosage using PE sequencing was feasible.

We next sequenced three maternal plasma samples (one with a female fetus and two from pregnancies each with a male fetus) collected in the third trimester.

Figure 12:
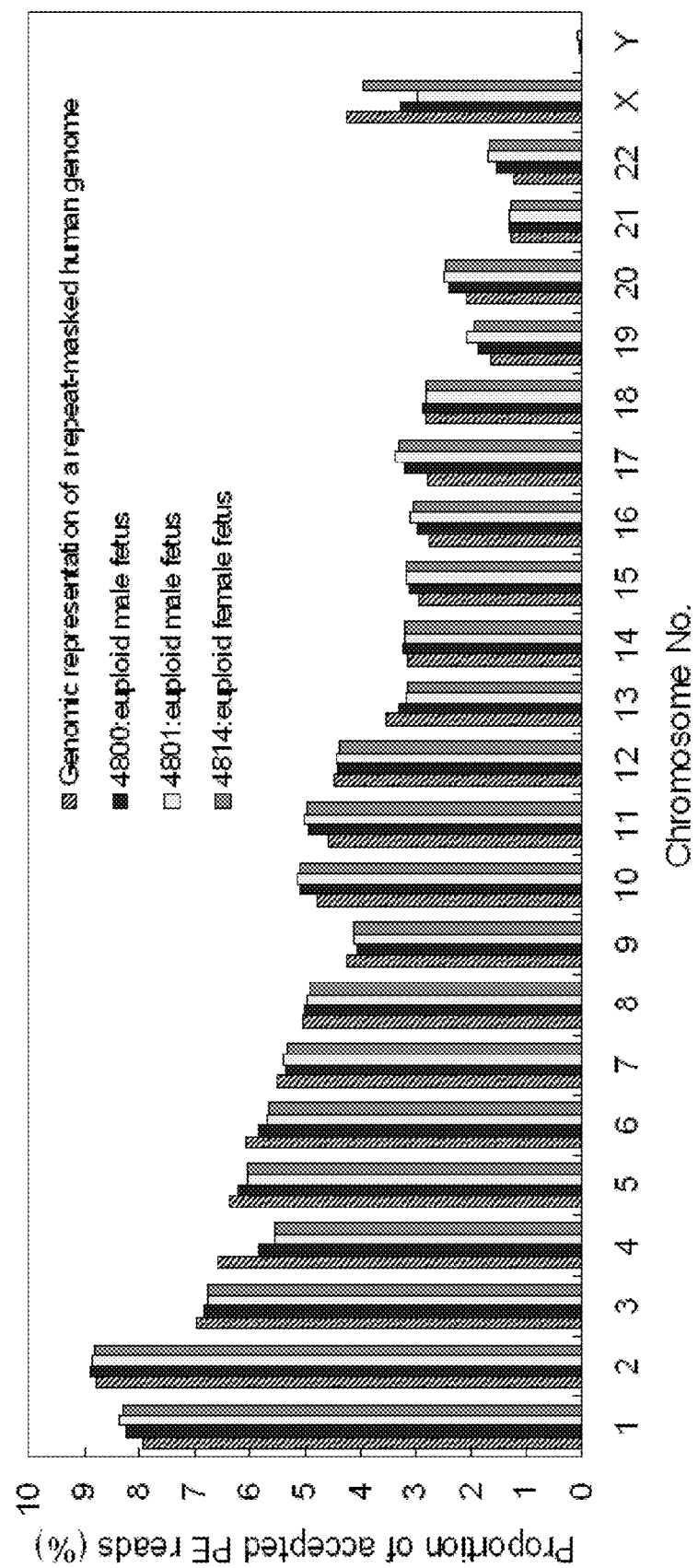
FIG. 12 shows a bar chart of proportion of accepted PE reads for each human chromosome for three maternal plasma samples collected in the third trimester according to an embodiment of the present invention.

FIG. 12 shows a bar chart of proportion of accepted PE reads for each human chromosome for three maternal plasma samples collected in the third trimester. The percentage of genomic representation of each chromosome as expected for a repeat-masked reference haploid female genome was plotted for comparison (stripped bars). The percentages of accepted PE reads mapped to each chromosome generally resembled the genomic representation expected for each chromosome in the human genome. Also, the absolute (and fractional) accepted PE counts mapped to chrY for the two pregnancies with male fetuses were 710 (0.064%) and 829 (0.079%), respectively, indicating positive detection of fetal DNA by PE sequencing of maternal plasma.

Sequencing and Alignment

Sequencing libraries were constructed from the extracted DNA using the Paired-End Sequencing Sample Preparation Kit (Illumina, San Diego, Calif.) mostly according to manufacturer's instructions. Since plasma DNA molecules are short fragments by nature, we omitted the steps of fragmentation and size selection by gel electrophoresis. DNA clusters were generated using an Illumina cluster station, followed by 36×2 cycles of sequencing on a Genome Analyzer II (Illumina).

The first 32 by from the 36 by sequenced reads were aligned to the repeat-masked human genome reference sequence (NCBI Build 36, version 48) using the Efficient Large-Scale Alignment of Nucleotide Databases for PE sequencing (elandpair) program (Illumina). As an illustration, we selected a subset of PE reads, namely those only PE reads meeting the following criteria, termed accepted PE reads, for subsequent analysis:
1) the individual members of each suggested pair were both sequenced on the same cluster position on the sequencing flow cell and could be aligned to the same chromosome with the correct orientation as expected for the reference human genome;
2) the sequenced reads of both members of the pair could be aligned to the repeat-masked reference human genome without any nucleotide mismatch;
3) the sequenced reads of each member of the pair had a uniqueness score >4;
4) pairs demonstrating an insert size less than 600 bp.

Approximately 1.6 million pairs (17% from a total of ±10 million sequenced molecules) of high quality sequenced reads, aligned uniquely to the repeat-masked reference human genome without mismatches, were obtained from each plasma sample. Alignment errors to chromosome Y were reduced among the accepted paired-end reads compared with unique reads obtained from single-read sequencing.

A small number of accepted PE reads were mapped to chrY in both the maternal plasma sample involving a female fetus (50 reads, 0.0047%) and the female T21 placental tissue (64 reads, 0.0044%). Only 38% of these sequences were confirmed by Basic Local Alignment Search Tool (BLAST) analysis to be uniquely mapped to chrY. Similarly, 150 PE reads aligned to chrY were randomly picked from each of the two plasma samples of pregnancies with male fetuses. 90.4% (135 of 150) and 98.0% (147 of 150) of the paired sequences could be aligned uniquely to chrY by BLAST. 150 paired sequences from each of the other human chromosomes were also randomly selected from each of the three maternal plasma samples for BLAST analysis. Almost all (98.1% for chromosomes 4 and 5, 100% for all other chromosomes) accepted PE reads mapped to the non-Y chromosomes were validated by BLAST to align uniquely and perfectly to the corresponding chromosomes with exactly the same insert size as indicated by the eland_pair output.

Our data suggested that a large proportion of the reads mapped to chrY in the female DNA samples were false-positive signals due to non-specific bioinformatics alignment. We reported a similar observation in our previous study using single read (SR) sequencing (Chiu et al. 2008, Proc Natl. Acad. Sci. USA, 105, 20458-63). We compared if SR or PE sequencing was more prone to produce such an artifact. For PE sequencing, the reads from the two ends of each DNA fragments are generated independently as read1 and read2, respectively, and are paired by post-sequencing bioinformatics. Therefore, read1 from the PE sequencing run could be analyzed as if it was SR sequencing. When analyzed as SR sequencing, the absolute (and fractional) U0-1-0-0 sequence reads mapped to chrY for the two female DNA samples described above were 147 (0.0094%) and 171 (0.0072%), respectively. This was almost doubled that of the corresponding accepted PE reads mapped to chrY.

As evident by the chrY data from the female samples, PE sequencing can attain higher alignment accuracy than SR sequencing. The number of nucleotides sequenced and therefore available for alignment from each plasma DNA molecule is doubled in PE compared with SR sequencing and thus, minimizes the chance of misalignment to other locations in the human genome. A positional requirement of not accepting pairs separated by too great a distance on the same chromosome is another way of reducing the chance of misalignment.

Identification of Trisomy 21 Fetus Using Paired-End Sequencing

Nine women each pregnant with a euploid fetus and four women each pregnant with a T21 fetus were recruited in the first and second trimesters. Direct noninvasive detection of fetal T21 from maternal plasma was attempted using PE sequencing. The 13 samples were processed separately in two PE sequencing runs. The clinical details and sequencing counts for each case are shown in Table 1 of FIG. 13. 8.3-10.5 million DNA molecules were sequenced from each case, of which a median of 1.6 million pairs (17% of total) passed the criteria to be deemed as accepted PE reads We expressed the number of accepted PE reads aligned to each chromosome as a proportion of all accepted PE reads generated for the sample. The mean and SD of the proportion of accepted PE reads for chromosomes 21 and X were established from the plasma samples of pregnancies with male euploid fetuses which were considered as the reference sample set. The z-score, referring to the number of standard deviations from the mean of a reference population, for each test sample was then calculated. A z-score greater than ±3 signifies a difference greater than the 99th percentile of the proportion of accepted PE reads of the euploid reference sample set for the target chromosome, i.e., a P value of 0.01.

Figure 14:
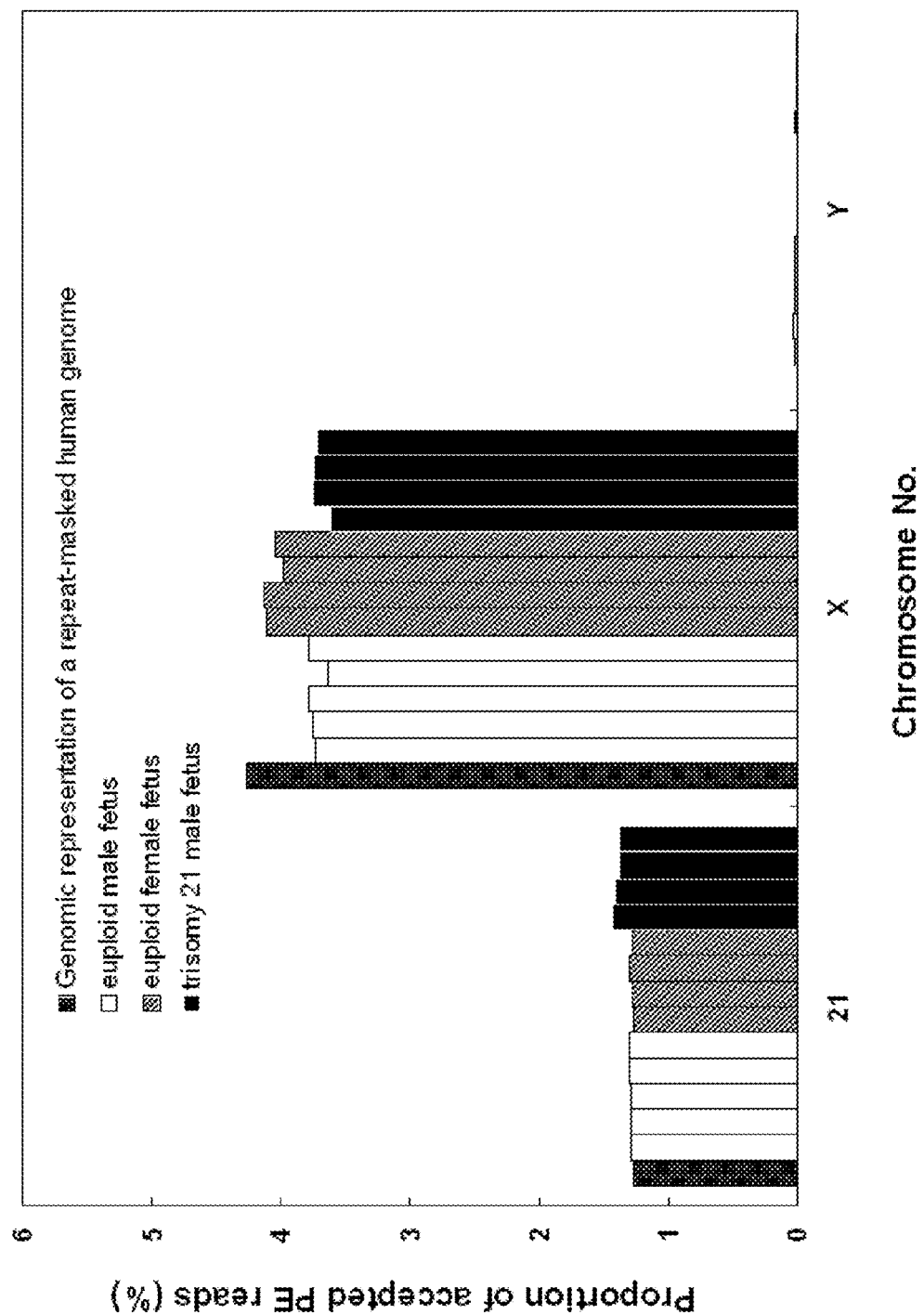
FIG. 14 is a bar chart of the proportion of accepted PE reads for chromosomes 21, X and Y for 13 early pregnancy maternal plasma samples according to an embodiment of the present invention.

FIG. 14 is a bar chart of the proportion of accepted PE reads for chromosomes 21, X and Y for 13 early pregnancy maternal plasma samples. The ranges of proportion of accepted PE reads for chromosome Y for three groups are 0.022-0.034% for the pregnancies with euploid male fetuses, 0.0048-0.0058% for pregnancies with euploid female fetuses and 0.029-0.038% for pregnancies with trisomy 21 male fetuses. FIG. 14 shows that the percentages of accepted PE reads aligned to chr21 were higher for all T21 than for euploid cases and the corresponding values for chrX were higher and those for chrY were lower for all female than male fetuses.

Five maternal plasma samples each carrying a euploid male fetus were selected as the reference group for the calculation of the z-scores. Z-scores were also calculated for the proportion of U0-1-0-0 reads from read1 of the PE sequencing run to simulate the data obtained when SR sequencing was performed. Z-scores of chr21 for the four T21 fetuses ranged from 5.63-8.89 for SR sequencing and ranged from 8.07-12.00 for PE sequencing. Z-scores of chrX for the four female fetuses ranged from 5.04-7.69 for SR sequencing and ranged from 3.91-6.35 for PE sequencing. There were no statistically significant differences in the z-scores for chromosomes 21 or X when comparing the PE and SR sequencing data (P=0.125, Wilcoxon signed-rank test).

Size Distribution of DNA Fragments in Maternal Plasma

The length of each DNA fragment was inferred from the data output of the eland_pair program by adding 32 by to the absolute positional offset between the chromosomal positions at the start of each member of the paired sequence reads. The awk utility of Linux was used to identify the paired reads with a size less than or equal to each of the analyzed size cutoffs.

We studied the size profile of plasma DNA molecules in the nine pregnant women carrying male fetuses among the 13 pregnancies described above as well as plasma from 2 adult males. For the maternal plasma samples, the reads mapped to chrY are of fetal origin while the reads for the other chromosomes are predominantly of maternal origin. We therefore analyzed the size profile of the reads on the Y and non-Y chromosomes independently.

Figure 15A:
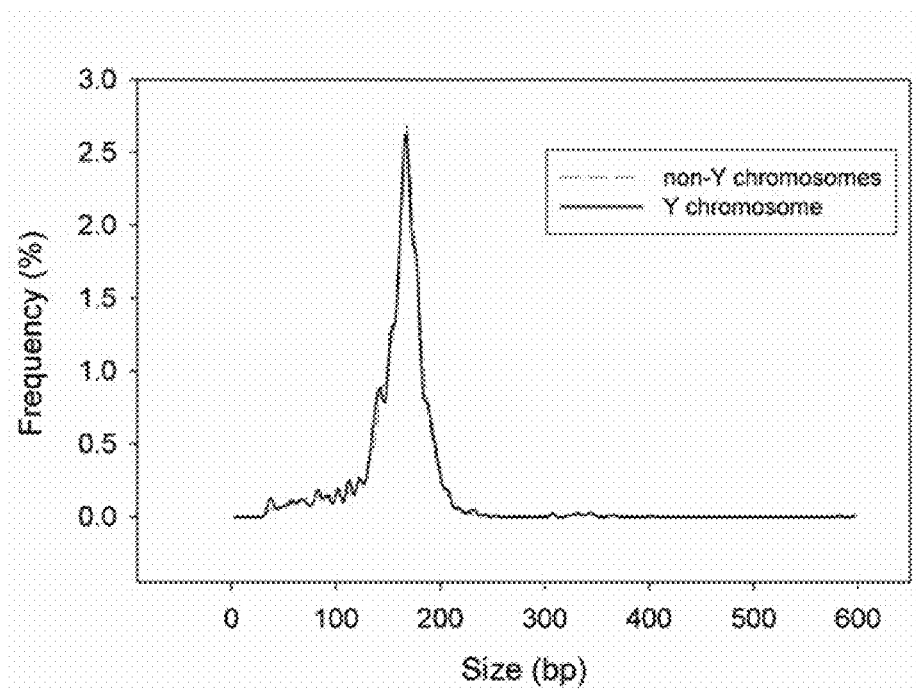
FIGS. 15A and 15B show representative results for the size distribution of nucleotide fragments for one adult male plasma sample and one maternal plasma, respectively.
Figure 15B:
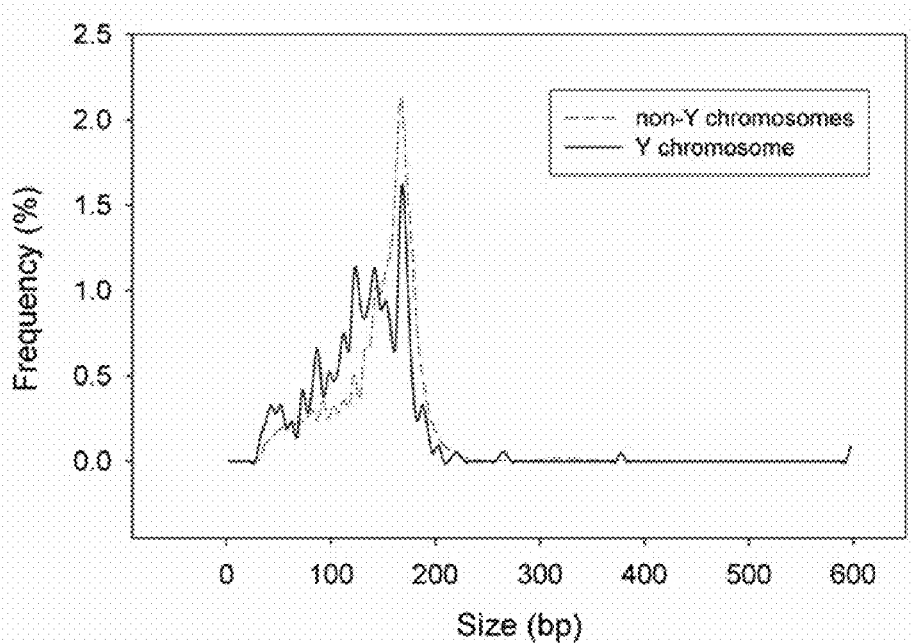

FIGS. 15A and 15B are histograms showing the size distributions of accepted PE reads aligned to Y (black line) and non-Y (dashed line) chromosomes in (A) the plasma from an adult male and (B) the plasma from a pregnant woman carrying a male fetus, respectively. The plasma DNA size distribution plots for the Y and non-Y chromosomes in each of the adult male samples were not statistically significantly different (P=0.118 and 0.134 respectively, Mann-Whitney rank-sum test). The plots peaked at 167 by and 168 bp, respectively, for the two adult male samples, being concordant with the insert sizes of the DNA libraries observed during bioanalyzer (Agilent) capillary electrophoresis.

For the maternal plasma samples, there was a clear demarcation between the size distribution curves for the Y and non-Y chromosomes (FIG. 15B). The median (range) length of the chrY fragments for the maternal plasma samples were 134 by (33 by to 378 bp) while that for the non-Y chromosomes were 157 by (33 by to 600 bp). The difference in size distribution between the Y and non-Y chromosomes for each maternal plasma sample was statistically significant (P<0.001, Mann-Whitney rank-sum test). The size distribution of DNA fragments varies for each chromosome.

Dependence of Fetal DNA on Size Selection

Figure 16:
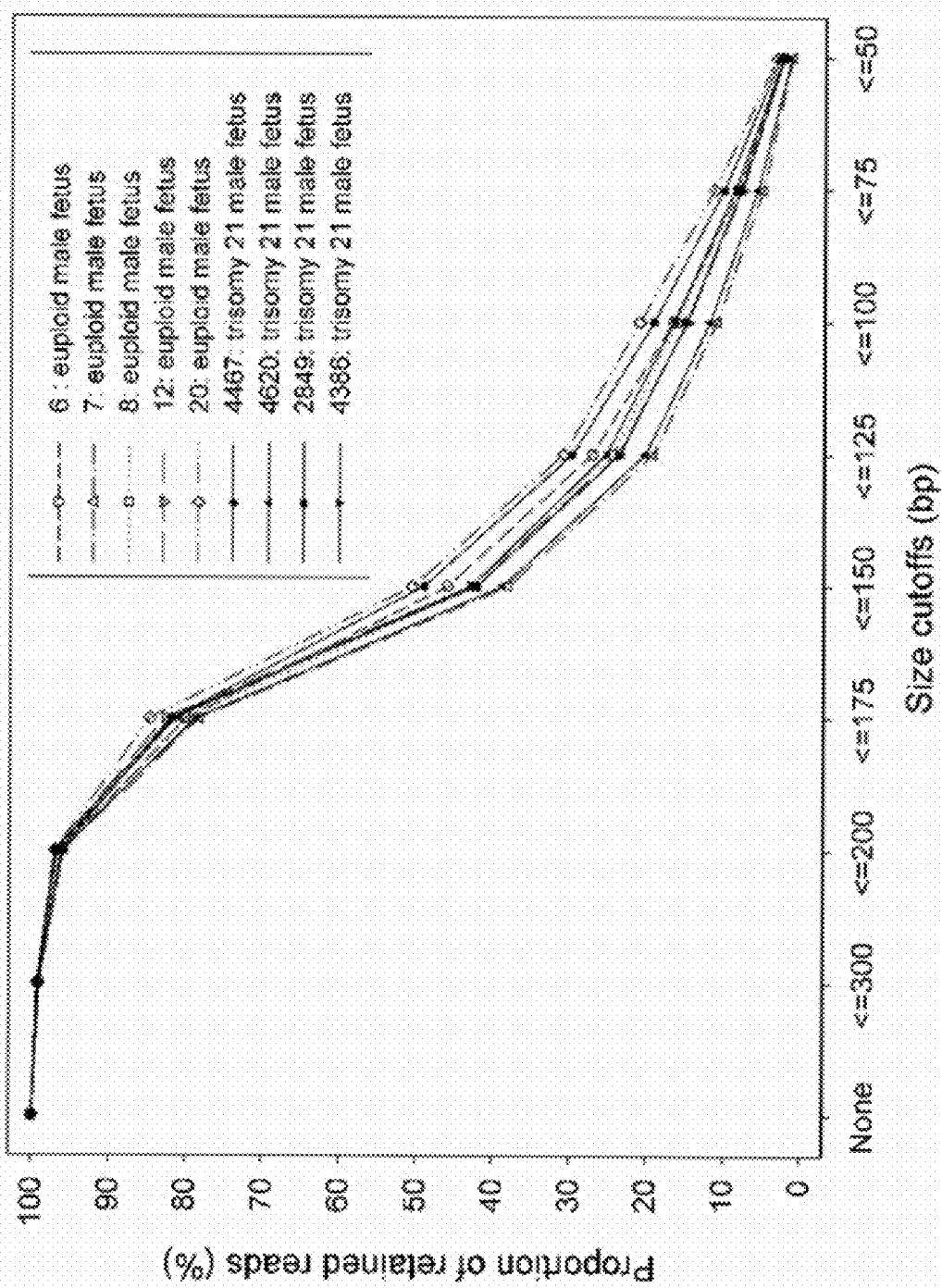
FIG. 16 is a plot showing the proportions of retained reads at a plurality of size cutoffs according to an embodiment of the present invention.

Cutoffs for DNA size were then used to achieve relative enrichment of fetal DNA in maternal plasma. We compared a series of selected cutoff points, including 300 bp, 200 bp, 175 bp, 150 bp, 125 bp, 100 bp, 75 by and 50 bp. The proportions of retained reads at each size cutoff are shown in FIG. 16.

Figure 17:
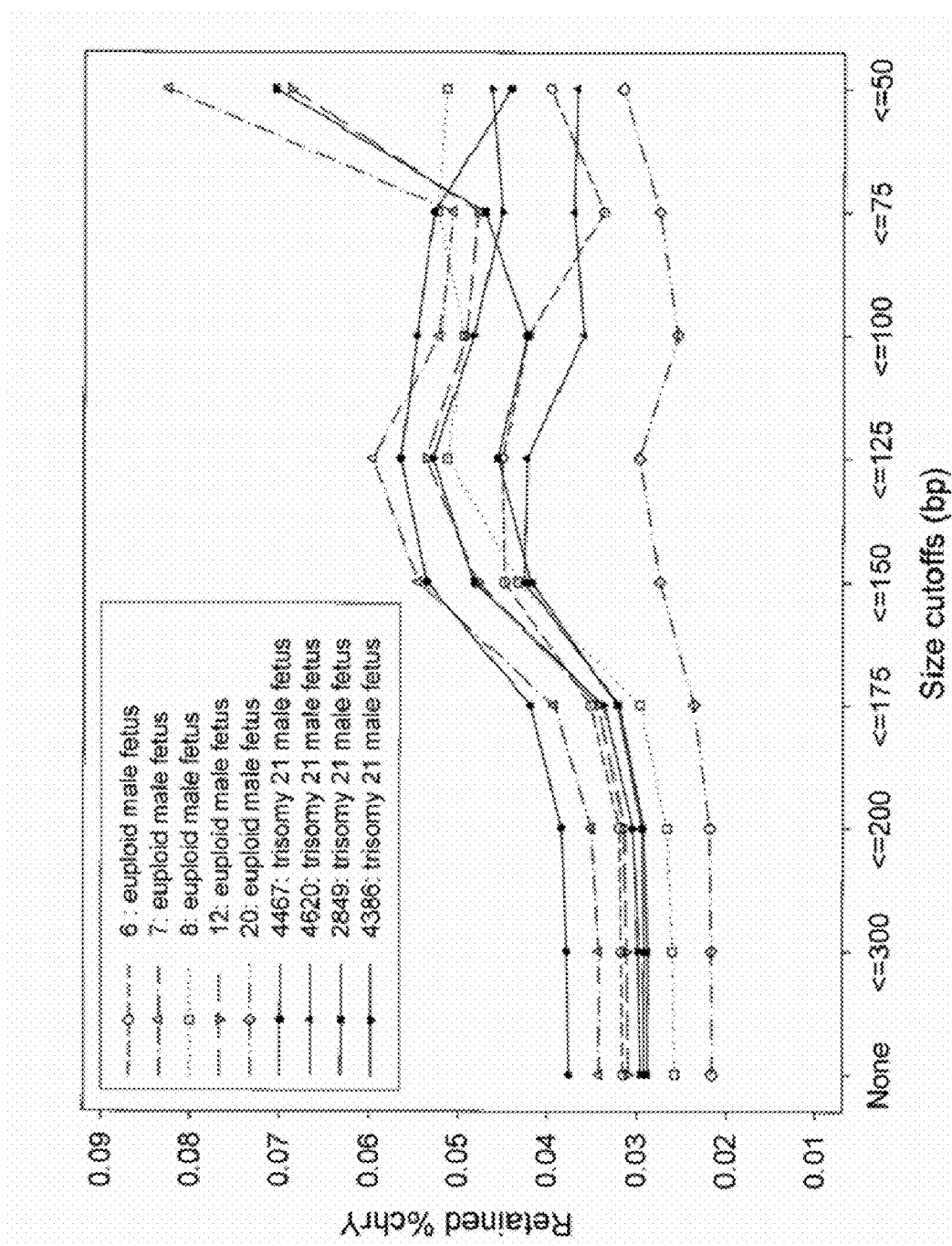
FIG. 17 shows the amount of retained reads from chrY as a proportion of all retained reads, termed retained % chrY according to an embodiment of the present invention.

FIG. 17 shows the amount of retained reads from chrY as a proportion of all retained reads, termed retained % chrY according to an embodiment of the present invention. The optimal balance between the degrees of fetal DNA enrichment achieved with a reasonable retention of accepted PE reads seemed to be achieved at the cutoff points of 175 by and 125 bp.

However, this balance is also affected by the actual detection of the overrepresentation. Fetal chromosomal aneuploidy could be detected more readily by maternal plasma analysis in samples with higher fractional fetal DNA concentrations (Lo et al., 2007, *Proc Natl Acad Sci USA*, 104, 13116-21. However, detection of overrepresentation of the aneuploid chromosome would be less precise when the absolute read number is reduced.

Figure 18A:
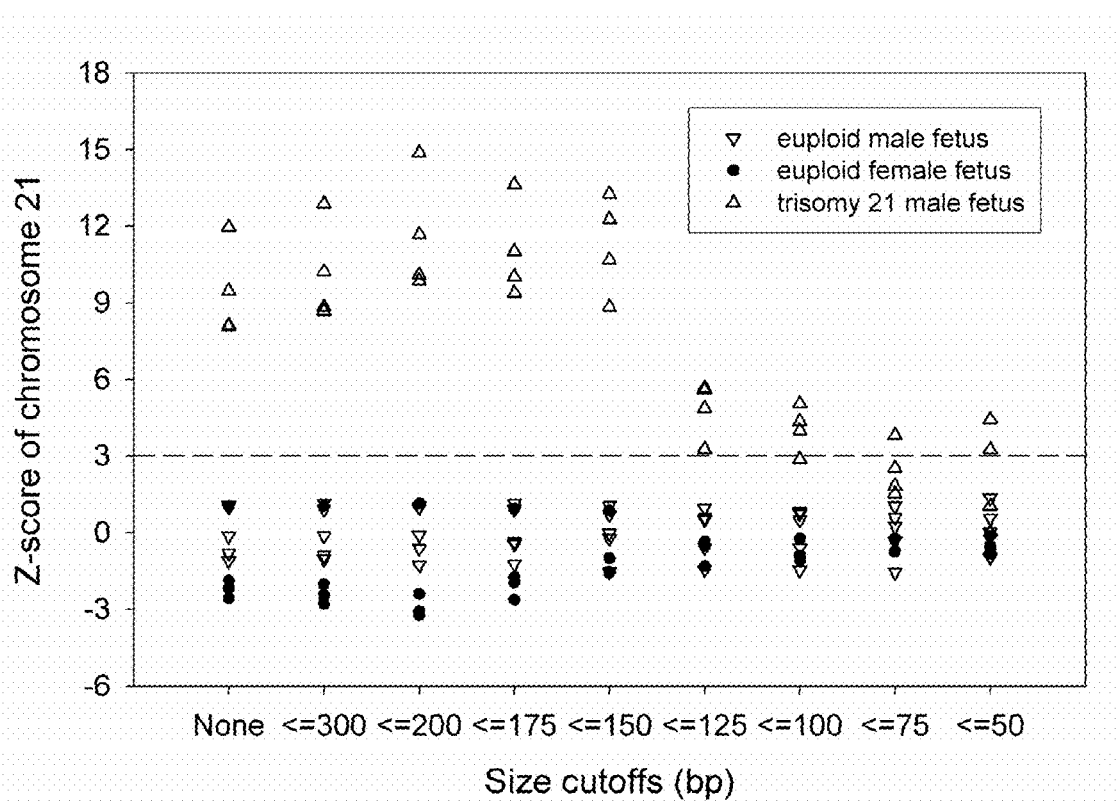
FIG. 18A shows the application of DNA size selection analysis for fetal trisomy 21 detection with a plot of the z-scores for chromosome 21 at each DNA size cutoff according to an embodiment of the present invention.

FIG. 18A shows the application of DNA size selection analysis for fetal trisomy 21 detection with a plot of the z-scores for chromosome 21 at each DNA size cutoff according to an embodiment of the present invention. The z-scores for chr21 for each of the size cutoffs are shown for different samples. The known status (male euploid, female euploid, and trisomy male) of each sample is provided by a symbol described in the legend. The horizontal dashed line refers to 3 standard devisions (SD) from the mean of the reference group.

A clearer demarcation in the z-scores of chr21 was achieved between the euploid and T21 cases when size cutoffs of 150 by or above were used, but at 125 by or less, the demarcation blurred (FIG. 18A). As stated before, the amount of retained chr21 is also important.

Figure 18B:
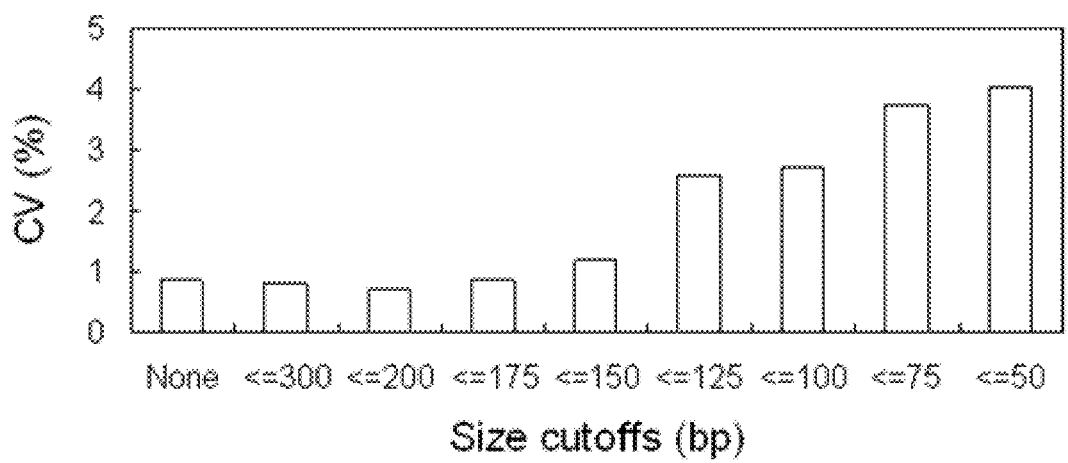
FIG. 18B is a histogram showing the coefficient of variation of measuring the proportion of retained chr21 reads at each size cutoff using the euploid cases according to an embodiment of the present invention.

FIG. 18B is a histogram showing the coefficient of variation (CV) (CV=SD/mean×100%) of measuring the proportion of retained chr21 reads at each size cutoff using the euploid cases according to an embodiment of the present invention. The CV increased substantially when a size cutoff of 125 by or less was used. Thus, FIGS. 18A and 18B confirm that a maximum length cutoff between 175 nucleotides to 125 nucleotides is optimal, which is counterintuitive to the notion that an increased percentage of fetal material is always better.

In summary, the median number of unique reads for PE sequencing, namely the accepted PE reads, was just 17% (~1.6 million reads) of the total sequenced reads while that for SR sequencing (U0-1-0-0 sequences of read1) of the same sample set was 26.4% (~2.5 million reads) of the total sequenced reads (FIG. 13). The difference was statistically significant (P<0.001, Wilcoxon signed-rank test). The latter data were similar to those (23.3%, ~2.4 million reads) reported in an earlier study where 28 maternal plasma samples were analyzed using SR sequencing (Chiu et al. 2008, *Proc Natl. Acad. Sci. USA*, 105, 20458-63).

The reduced number of unique read count for PE sequencing is possibly because of the more stringent definition of uniqueness whereby both reads in a pair, i.e. 64 bp, would need to align to the reference human genome without mismatches. Despite the reduced number of unique sequences, PE sequencing of maternal plasma DNA allowed the detection of fetal DNA and the assessment of fetal chromosome dosage, particularly when proper size selection was used.

We showed that one could selectively analyze the shorter sequences at the post-sequencing stage. Selective analysis of plasma DNA sequences shorter than a specified size cutoff would indeed increase the proportion of fetal derived sequences, but at a reduction in the absolute number of retained sequences. The reduced total number of sequenced reads renders the measurement of the representation of chr21 less precise (FIG. 18A).

There is therefore a tradeoff between the extent of fetal DNA enrichment and reduction in overall retained reads when any particular size cutoff value is used. When a maximum cutoff (i.e. length <=cutoff) is used, the optimal value for the cutoff is between 175 and 125 nt. As mentioned above, a minimum length may also be imposed.

The effects of the chosen size cutoff is also reflected in the CV for the measurement of the representation of chr21. Less precise measurements, reflected by a larger CV (FIG. 18B), result in larger SDs and thus reduce the z-score demarcation between the aneuploid and euploid cases. Thus, counterintuitively one cannot achieve the highest possible diagnostic accuracy simply by simply enriching for fetal DNA sequences maximally by selecting the shortest size cutoffs, as FIG. 17 would suggest.

Also, by knowing the detailed size profile of DNA molecules in maternal plasma, we could objectively predict the effects of fetal DNA enrichment based on size selection of the shorter sequences. The size selection using physical means, such as gel electrophoresis, may be performed based on the determined size profile, and may be done in addition to the post-sequencing selection.

In conclusion, paired-end sequencing of maternal plasma DNA permits fetal aneuploidy detection and also provides high resolution size profiles of fetal and maternal DNA in maternal plasma. Apart from using the Illumina Genome Analyzer (i.e. Solexa) technology for such paired-end sequencing, one could also use other high throughput DNA sequencing platform, e.g. the SOLiD technology from Applied Biosystems, part of Life Technologies and the Helicos True Single Molecule DNA sequencing technology (Harris T D et al. 2008 Science, 320, 106-109). One can also achieve the same goal by using the Roche 454 sequencing technology which can sequence whole DNA fragments in the target biological samples. Apart from trisomy 21 which has been used here as an example of chromosomal aneuploidy, one can also apply the technology developed here for the detection of aneuploidy involving chromosomes 13, 18, X and Y, e.g. trisomy 13, trisomy 18 and the sex chromosome aneuploidies.

IV. Determination of Number of Sequences Required

The sequencing result of the plasma DNA from a pregnant woman carrying a euploid male fetus is used for this analysis. The number of sequenced tags that can be mapped without mismatches to the reference human genome sequence was 1,990,000. Subsets of sequences were randomly chosen from these 1,990,000 tags and the percentage of sequences aligned to chromosome 21 was calculated within each subset. The number of sequences in the subsets was varied from 60,000 to 540,000 sequences. For each subset size, multiple subsets of the same number of sequenced tags were compiled by random selection of the sequenced tags from the total pool until no other combination was possible. The mean percentage of sequences aligned to chromosome 21 and its standard deviation (SD) were then calculated from the multiple subsets within each subset size. These data were compared across different subset sizes to determine the effect of subset size on the distribution of the percentage of sequences aligned to the chromosome 21. The $5^{th}$ and $95^{th}$ percentiles of the percentages were then calculated according to the mean and SD.

When a pregnant woman is carrying a trisomy 21 fetus, the sequenced tags aligned to chromosome 21 should be over-represented in the maternal plasma due to an extra dose of chromosome 21 from the fetus. The degree of over-representation is dependent on the fetal DNA percentage in the maternal plasma DNA sample following the equation below:

$$Per_{T21}=Per_{Eu}\times(1+f/2)$$

where
$Per_{T21}$ represents the percentage of sequences aligned to chromosome 21 in a woman with a trisomy 21 fetus; and
$Per_{Eu}$ represents the percentage of sequences aligned to chromosome 21 in a woman with a euploid fetus; and
f represents the fetal DNA percentage in maternal plasma DNA As shown in FIG. 7, the SD for the percentages of sequences aligned to chromosome 21 decreases with increasing number of sequences in each subset. Therefore, when the number of sequences in each subset increases, the interval between the $5^{th}$ and $95^{th}$ percentiles decreases. When the 5%-95% interval for the euploid and trisomy 21 cases do not overlap, then the differentiation between the two groups of cases would be possible with an accuracy of >95%.

As shown in FIG. 7, the minimal subset size for the differentiation of trisomy 21 cases from euploid cases is dependent on the fetal DNA percentage. The minimal subset sizes for differentiating trisomy 21 from euploid cases were 120,000, 180,000 and 540,000 sequences for fetal DNA percentages of 20%, 10% and 5%, respectively. In other words, the number of sequences needed to be analyzed would be 120,000 for determining whether a fetus has trisomy 21 when a maternal plasma DNA sample contains 20% fetal DNA. The number of sequences needed to be analyzed would be increased to 540,000 when the fetal DNA percentage drops to 5%.

As the data were generated using 36 basepair sequencing, 120,000, 180,000 and 540,000 sequences correspond to 0.14%, 0.22% and 0.65% of the human genome, respectively. As the lower range of fetal DNA concentrations in maternal plasma obtained from early pregnancies were reported to be some 5% (Lo, Y M D et al. 1998 Am J Hum Genet 62, 768-775), the sequencing of about 0.6% of the human genome may represent the minimal amount of sequencing required for diagnosis with at least 95% accuracy in detecting fetal chromosomal aneuploidy for any pregnancy.

V. Random Sequencing

To illustrate that the sequenced DNA fragments were randomly selected during the sequencing run, we obtained the sequenced tags generated from the eight maternal plasma samples analyzed in example I. For each maternal plasma specimen, we determined the starting positions in relation to the reference human genome sequence, NCBI assembly 36, of each of the 36 by sequenced tags that were aligned uniquely to chromosome 21 without mismatches. We then ordered the starting position number for the pools of aligned sequenced tags from each specimen in ascending order. We performed a similar analysis for chromosome 22. For illustrative purpose, the top ten starting positions for chromosome 21 and chromosome 22 for each of the maternal plasma specimens are shown in FIGS. 8A and 8B, respectively. As can be appreciated from these Tables, the sequenced pools of DNA fragments were non-identical between samples.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

Figure 9:
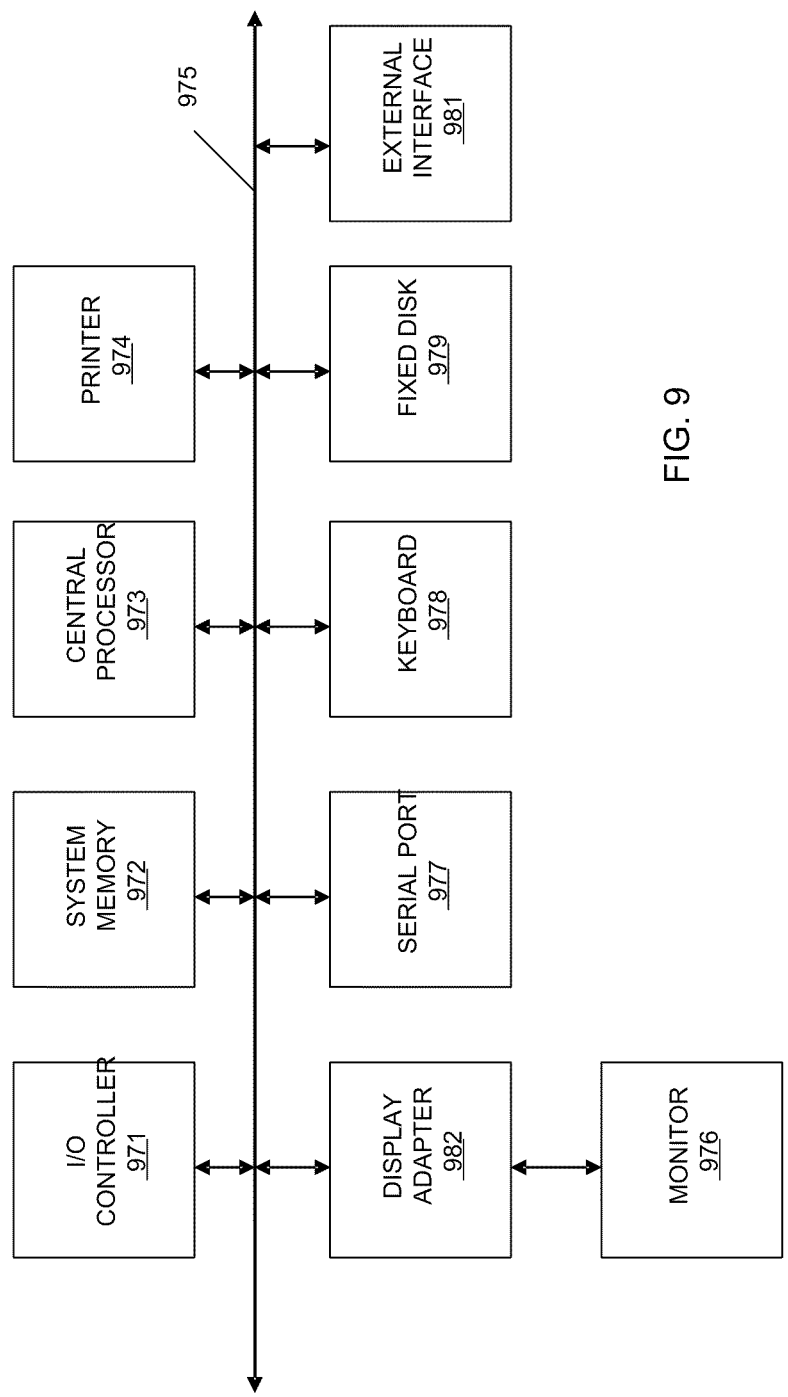
FIG. 9 shows a block diagram of an exemplary computer apparatus usable with system and methods according to embodiments of the present invention.

An example of a computer system is shown in FIG. 9. The subsystems shown in FIG. 9 are interconnected via a system bus 975. Additional subsystems such as a printer 974, keyboard 978, fixed disk 979, monitor 976, which is coupled to display adapter 982, and others are shown. Peripherals and input/output (I/O) devices, which couple to I/O controller 971, can be connected to the computer system by any number of means known in the art, such as serial port 977. For example, serial port 977 or external interface 981 can be used to connect the computer apparatus to a wide area network such as the Internet, a mouse input device, or a scanner. The interconnection via system bus allows the central processor 973 to communicate with each subsystem and to control the execution of instructions from system memory 972 or the fixed disk 979, as well as the exchange of information between subsystems. The system memory 972 and/or the fixed disk 979 may embody a computer readable medium.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

The present application is related to concurrently filed non-provisional application entitled "DETERMINING A NUCLEIC ACID SEQUENCE IMBALANCE," Ser. No. 12/178,116 the entire contents of which are herein incorporated by reference for all purposes.

All publications, patents, and patent applications cited herein are hereby incorporated by reference in their entirety for all purposes.

What is claimed is:

1. A method for determining presence or absence of fetal aneuploidy in a fetus by analyzing a biological sample from a female pregnant with the fetus, the biological sample comprising a mixture of fetal DNA from the genome of the fetus and DNA from the genome of the pregnant female, wherein the method comprises:
   a. conducting random sequencing of DNA fragments from the mixture to determine sequences of said DNA fragments, said DNA fragments including fragments from the genome of the pregnant female and fragments from the genome of the fetus;
   b. identifying chromosomes to which the sequences obtained in step a) belong, wherein b) includes aligning the sequences to a human genome, and wherein which part of the human genome that the sequences are aligned is not pre-determined;
   c. using data of step b) to compare a first amount of sequences from at least one first chromosome in said mixture to a second amount of sequences from a second chromosome in said mixture, thereby determining the presence or absence of said fetal aneuploidy, wherein the second amount is determined from a pool of sequences that align to a plurality of positions on the second chromosome, and wherein the first amount is determined from a pool of sequences that align to a plurality of positions on the at least one first chromosome.

2. The method of claim 1 wherein said biological sample is a plasma sample.

3. The method of claim 1, wherein conducting random sequencing comprises i) capturing the DNA fragments on a surface; ii) clonally expanding the captured DNA fragments to create a flow cell, and iii) sequencing of the clonally-expanded DNA fragments in the flow cell by a DNA sequencing by synthesis process.

4. The method of claim 1, further comprising:
   sub-selecting, from the biological sample, DNA fragments from the at least one first chromosome and the second chromosome to obtain an enriched pool of DNA fragments, wherein the random sequencing is performed on the enriched pool of DNA fragments.

5. The method of claim 1, wherein the biological sample is blood, plasma, serum, urine or saliva.

6. The method of claim 1, wherein the sequences identified as belonging to the second chromosome uniquely align to the second chromosome without mismatches.

7. The method of claim 1, wherein the nucleic acid molecules sequenced by random sequencing represent a portion of the human genome selected from the group consisting of at least about 0.1%, 0.5%, 1%, 5%, 10%, 20% and 30% of the human genome.

8. The method of claim 7, wherein the human genome is repeat-masked.

9. The method of claim 1, wherein the second chromosome is chromosome 21, chromosome 18, chromosome 13, chromosome X, or chromosome Y.

10. The method of claim 1, wherein comparing the first amount to the second amount includes:
    determining a parameter from the first amount and the second amount, wherein the parameter represents a relative amount between the first amount and the second amount; and
    comparing the parameter to one or more cutoff values to determine the presence or absence of said fetal aneuploidy.

11. The method of claim 10, wherein at least one of the cutoff values represents a reference value established from one or more normal biological samples.

12. The method of claim 10, wherein the parameter is a ratio of the second amount to the second amount plus the first amount.

13. The method of claim 10, wherein the one or more cutoff values take into account a size of the second chromosome relative to a size of the at least one first chromosome.

14. A computer program product comprising a computer readable medium encoded with a plurality of instructions for controlling a computing system to perform an operation for determining presence or absence of fetal aneuploidy in a fetus by analyzing a biological sample from a female pregnant with the fetus, the biological sample comprising a mixture of fetal DNA from the genome of the fetus and DNA from the genome of the pregnant female, the instructions comprising:
- a. receiving sequences obtained from random sequencing of DNA fragments from said mixture, said DNA fragments including fragments from the genome of the pregnant female and fragments from the genome of the fetus;
- b. identifying chromosomes to which the sequences received in step a) belong, wherein step b) includes aligning the sequences to a human genome, and wherein which part of the human genome that the sequences are aligned is not pre-determined;
- c. using data of step b) to compare a first amount of sequences from at least one first chromosome in said mixture to a second amount of sequences from a second chromosome in said mixture, thereby determining the presence or absence of said fetal aneuploidy, wherein the second amount is determined from a pool of sequences that align to a plurality of positions on the second chromosome, and wherein the first amount is determined from a pool of sequences that align to a plurality of positions on the at least one first chromosome.

15. The computer program product of claim 14, wherein the sequences identified as belonging to the second chromosome uniquely align to the second chromosome without mismatches.

16. The computer program product of claim 14, wherein comparing the first amount to the second amount includes:
   determining a parameter from the first amount and the second amount, wherein the parameter represents a relative amount between the first amount and the second amount; and
   comparing the parameter to one or more cutoff values to determine the presence or absence of said fetal aneuploidy.

17. The computer program product of claim 16, wherein at least one of the cutoff values represents a reference value established from one or more normal biological samples.

18. The computer program product of claim 16, wherein the one or more cutoff values take into account a size of the second chromosome relative to a size of the at least one first chromosome.

19. The computer program product of claim 16, wherein the parameter is a ratio of the second amount to the second amount plus the first amount.

20. The computer program product of claim 14, wherein said biological sample is a plasma sample.

21. The computer program product of claim 14, wherein the biological sample is blood, plasma, serum, urine or saliva.

22. The computer program product of claim 14, wherein the random sequencing comprises i) capturing the DNA fragments on a surface; ii) clonally expanding the captured DNA fragments to create a flow cell, and iii) sequencing of the clonally-expanded DNA fragments in the flow cell by a DNA sequencing by synthesis process.

23. The computer program product of claim 14, wherein the sequences obtained from random sequencing represent a portion of the human genome selected from the group consisting of at least about 0.1%, 0.5%, 1%, 5%, 10%, 20% and 30% of the human genome.

24. The computer program product of claim 23, wherein the human genome is repeat-masked.

25. The computer program product of claim 14, wherein the second chromosome is chromosome 21, chromosome 18, chromosome 13, chromosome X, or chromosome Y.

* * * * *